(12) United States Patent
Kim et al.

(10) Patent No.: US 9,028,978 B2
(45) Date of Patent: May 12, 2015

(54) COMPOUND AND ORGANIC LIGHT-EMITTING DEVICE INCLUDING THE SAME

(75) Inventors: Myeong-Suk Kim, Yongin (KR); Dong-Woo Shin, Yongin (KR); Sung-Soo Bae, Yongin (KR); Ji-Hye Shim, Yongin (KR); Dae-Yup Shin, Yongin (KR); Byoung-Ki Choi, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 522 days.

(21) Appl. No.: 13/309,650

(22) Filed: Dec. 2, 2011

(65) Prior Publication Data

US 2012/0326133 A1  Dec. 27, 2012

(30) Foreign Application Priority Data

Jun. 22, 2011  (KR) ........................ 10-2011-0060809

(51) Int. Cl.

| | |
|---|---|
| *H01L 51/54* | (2006.01) |
| *C07D 403/10* | (2006.01) |
| *C07D 401/10* | (2006.01) |
| *C07C 211/61* | (2006.01) |
| *C07C 255/58* | (2006.01) |
| *H01L 51/00* | (2006.01) |
| *C07D 209/86* | (2006.01) |
| *C09K 11/06* | (2006.01) |
| *H05B 33/10* | (2006.01) |
| *H01L 51/50* | (2006.01) |

(52) U.S. Cl.
CPC ............ *H01L 51/006* (2013.01); *C07C 255/58* (2013.01); *C07C 211/61* (2013.01); *C07D 209/86* (2013.01); *C09K 11/06* (2013.01); *H01L 51/0055* (2013.01); *H01L 51/0059* (2013.01); *H01L 51/0072* (2013.01); *H01L 51/0077* (2013.01); *H01L 51/0081* (2013.01); *H01L 51/5012* (2013.01); *H05B 33/10* (2013.01); *C09K 2211/1007* (2013.01); *C09K 2211/1011* (2013.01); *C09K 2211/1014* (2013.01)

(58) Field of Classification Search
None
See application file for complete search history.

(56) References Cited

U.S. PATENT DOCUMENTS

| 2009/0008605 A1 | 1/2009 | Kawamura et al. |
|---|---|---|
| 2009/0009065 A1 | 1/2009 | Nishimura et al. |
| 2009/0009066 A1 | 1/2009 | Nishimura et al. |

FOREIGN PATENT DOCUMENTS

KR  1020100042271 A  4/2010

*Primary Examiner* — J. L. Yang
(74) *Attorney, Agent, or Firm* — Robert E. Bushnell, Esq.

(57) ABSTRACT

A compound represented by Formula 1 below and an organic light-emitting device including an organic layer containing the compound of Formula 1:

Formula 1

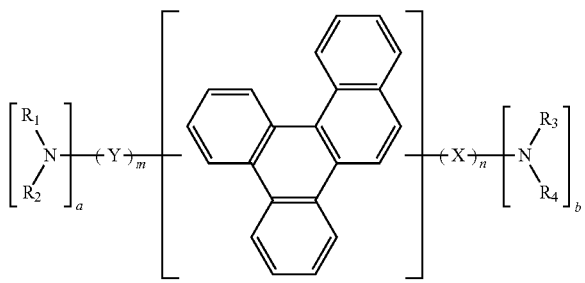

wherein $R_1$ to $R_4$, X and Y, a and b, and m and n are defined as in the specification.

18 Claims, 1 Drawing Sheet

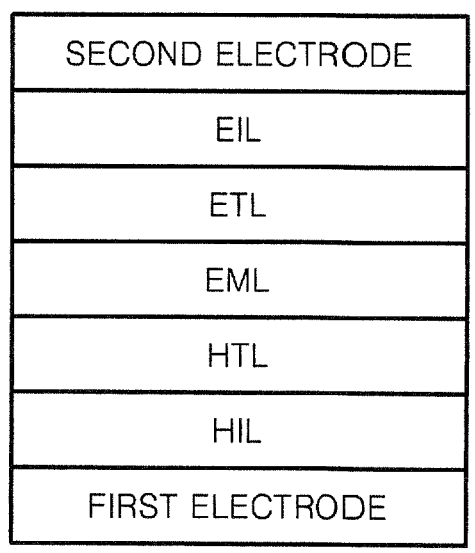

COMPOUND AND ORGANIC LIGHT-EMITTING DEVICE INCLUDING THE SAME

CROSS-REFERENCE TO RELATED PATENT APPLICATION

This application makes reference to, incorporates the same herein, and claims all benefits accruing under 35 U.S.C. §119 from an application earlier filed in the Korean Intellectual Property Office on 22 Jun. 2011, and there duly assigned Serial No10-2011-0060809.

BACKGROUND OF THE INVENTION

1. Field of the Invention

The present invention relates to a compound represented by Formula 1 or Formula 2 and an organic light-emitting device including the compound.

2. Description of the Related Art

Light-emitting devices are self-emission type display devices and have a wide viewing angle, a high contrast ratio, and a short response time. Due to these characteristics, light-emitting devices are drawing more attention. Such light-emitting devices can be roughly classified into inorganic light-emitting devices that include emission layers containing inorganic compounds, and organic light-emitting devices that include emission layers containing organic compounds. Specifically, organic light-emitting devices have higher luminance, lower driving voltages, and shorter response times than inorganic light-emitting devices, and can render multicolored displays. Thus, much research into such organic light-emitting devices has been conducted. Typically, an organic light-emitting device has a stack structure including an anode, a cathode and an organic emission layer interposed therebetween. However, a hole injection layer and/or a hole transport layer may be further stacked between the anode and the organic emission layer, and/or an electron transport layer may be further stacked between the organic emission layer and the cathode. In other words, an organic light-emitting device may have a stack structure of anode/hole transport layer/organic emission layer/cathode or a stack structure of anode/hole transport layer/organic emission layer/electron transport layer/cathode.

As a material for forming the organic emission layer, anthracene derivatives can be used. However, organic light-emitting devices including such materials may not have satisfactory life span, efficiency, and power consumption characteristics, thereby improvement in this regard still being necessary.

SUMMARY OF THE INVENTION

The present invention provides a novel compound with an improved luminescent efficiency and color purity.

The present invention provides an organic light-emitting device including the compound.

According to an aspect of the present invention, there is provided a compound represented by Formula 1 below:

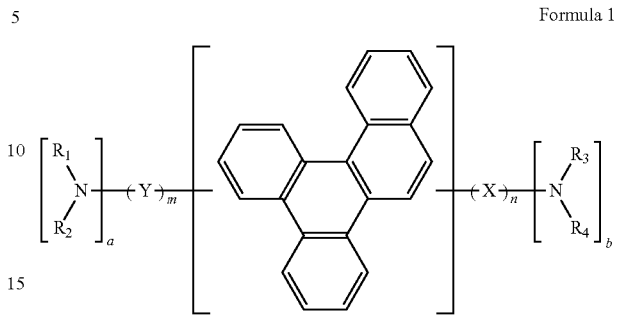

Formula 1 wherein in Formula 1, X and Y may be each independently selected from the group consisting of a substituted or unsubstituted $C_6$-$C_{60}$ arylene group, a substituted or unsubstituted $C_4$-$C_{60}$ heteroarylene group, a substituted or unsubstituted $C_5$-$C_{60}$ cycloalkylene group, and a substituted or unsubstituted $C_5$-$C_{60}$ heterocycloalkylene group;

$R_1$ to $R_4$ may be each independently selected from the group consisting of a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ aryl group, a substituted or unsubstituted $C_4$-$C_{60}$ heteroaryl group, a substituted or unsubstituted $C_6$-$C_{60}$ condensed polycyclic group, a halogen atom, a cyano group, a nitro group, a hydroxyl group, and a carboxyl group;

adjacent $R_1$ and $R_2$ or $R_3$ and $R_4$ may be optionally linked together to form a saturated or unsaturated carbon ring;

m, and n may be each independently an integer from 0 to 2; and a and b may be each independently an integer from 0 to 2 with a proviso that both a and b cannot be zero at the same time.

In some embodiments, X and Y in Formula 1 may be each independently selected from the group consisting of a substituted or unsubstituted $C_6$-$C_{30}$ arylene group, a substituted or unsubstituted $C_4$-$C_{20}$ heteroarylene group, a substituted or unsubstituted $C_5$-$C_{20}$ cycloalkylene group, and a substituted or unsubstituted $C_5$-$C_{20}$ heterocycloalkylene group; and $R_1$ to $R_4$ may be each independently selected from the group consisting of a hydrogen atom, a deuterium atom, a cyano group, a halogen atom, a substituted or unsubstituted $C_1$-$C_{20}$ alkyl group, a substituted or unsubstituted $C_6$-$C_{40}$ aryl group, a substituted or unsubstituted $C_4$-$C_{40}$ heteroaryl group, and a substituted or unsubstituted $C_6$-$C_{40}$ condensed polycyclic group.

In some embodiments, X and Y in Formula 1 may be each independently selected from groups represented by Formulae 2a to 2d below:

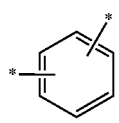

2a

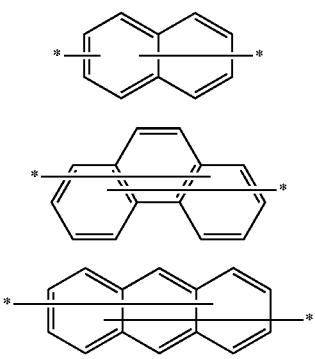

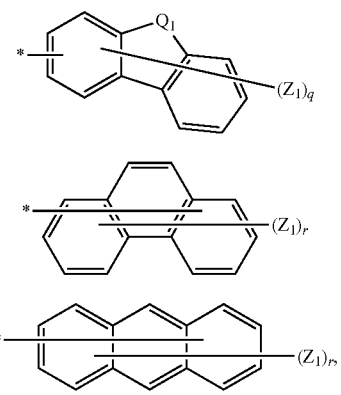

wherein in Formulae 2a to 3d, * may indicate a binding site.

In some embodiments $R_1$ to $R_4$ in Formula 1 may be each independently selected from the group consisting of a hydrogen atom, a deuterium atom, a $C_1$-$C_{20}$ alkyl group, and groups represented by Formulae 3a to 3e below:

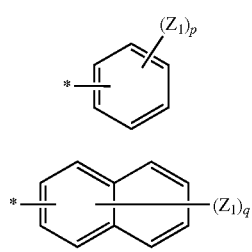

wherein in Formulae 3a to 3e, $Q_1$ may be a linking group represented by —C($R_5$)($R_6$)—, —N($R_7$)—, —S—, or —O—;

$Z_1$, $R_5$, $R_6$, and $R_7$ may be independently selected from the group consisting of a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_4$-$C_{20}$ heteroaryl group, a substituted or unsubstituted $C_6$-$C_{20}$ condensed polycyclic group, a halogen atom, a cyano group, a nitro group, a hydroxyl group, and a carboxyl group;

p may be an integer from 1 to 5; q may be an integer from 1 to 7; r may be an integer from 1 to 9; and

* may indicate a binding site.

In some embodiments the compound of Formula 1 may include one of the compounds below:

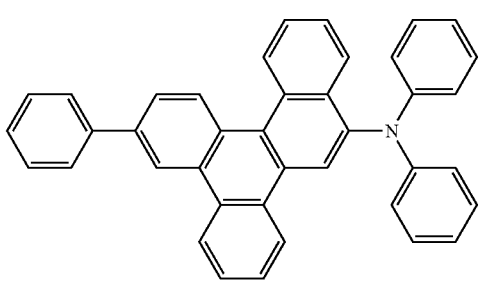

1

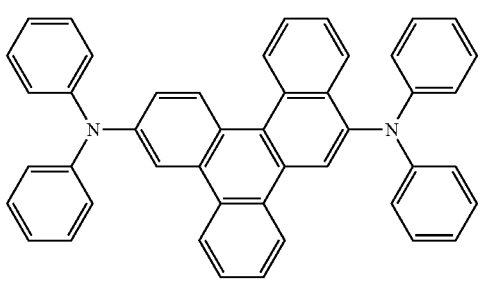

2

-continued
3
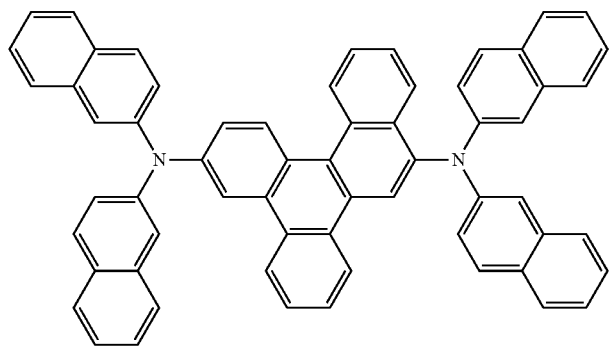
4
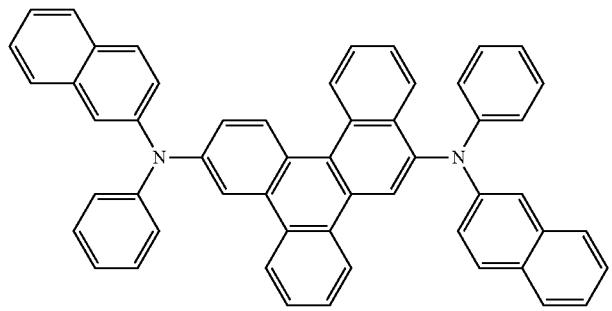
5
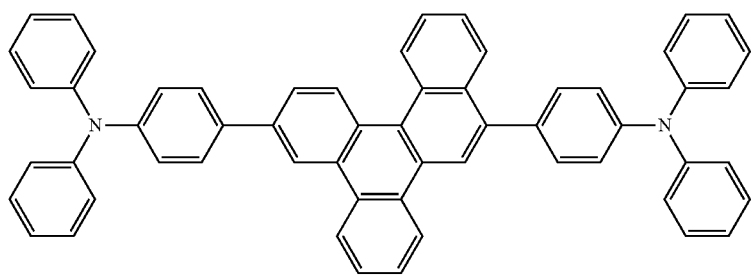
6
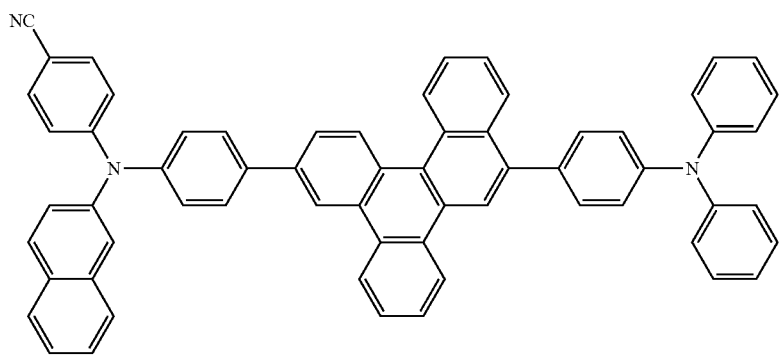
7
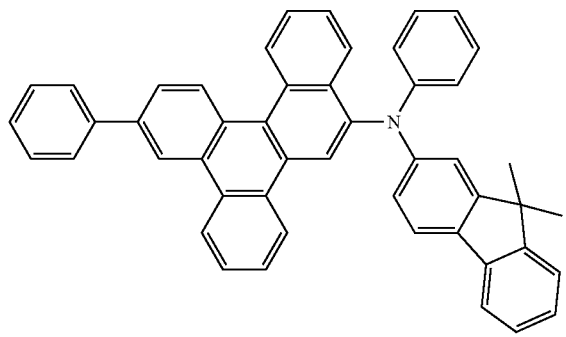

8
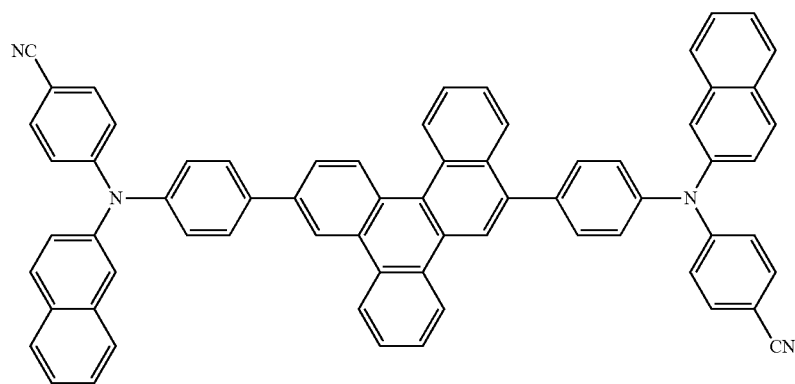
9
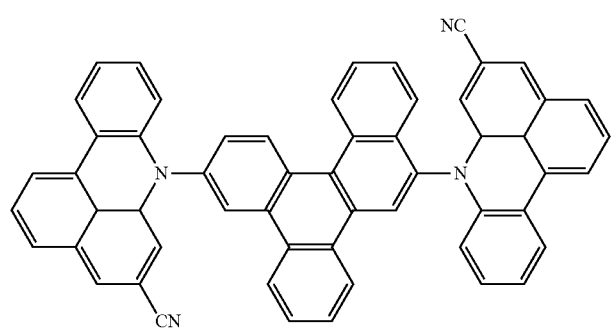
10
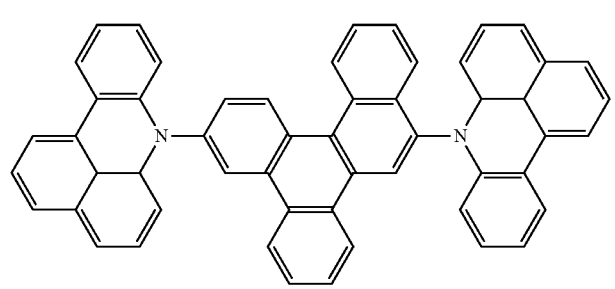
11
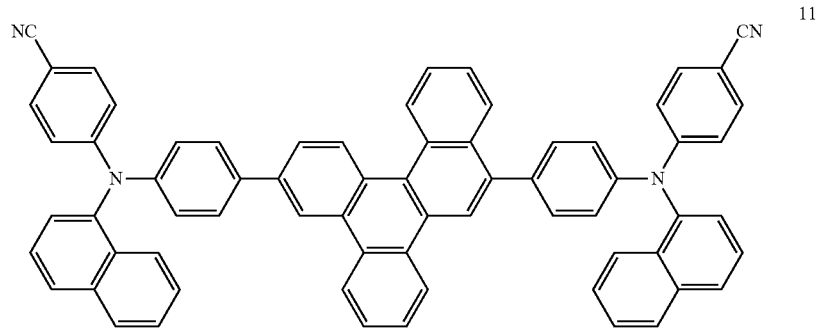
12
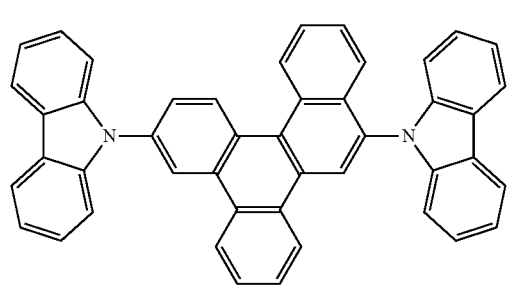

-continued
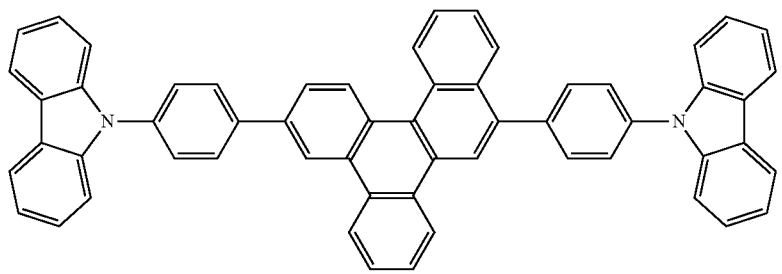
13
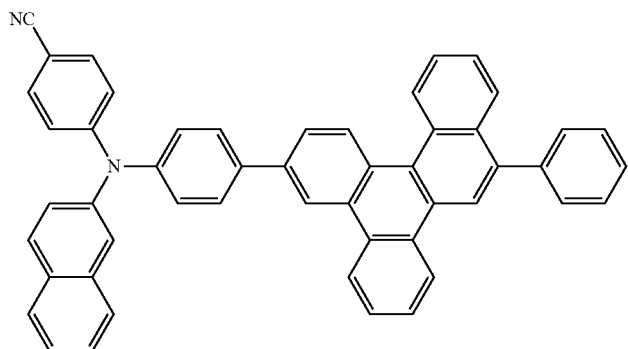
14
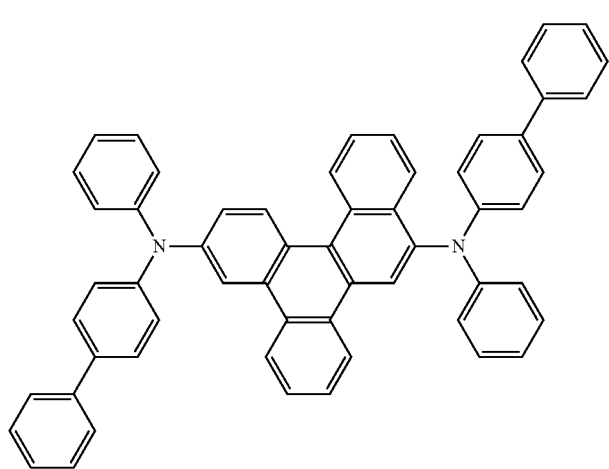
15
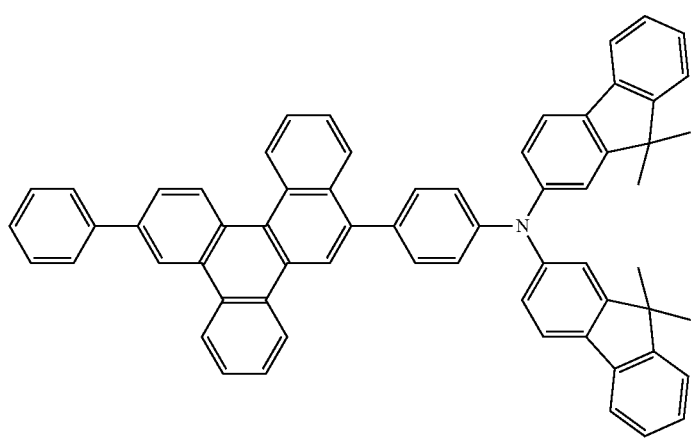
16

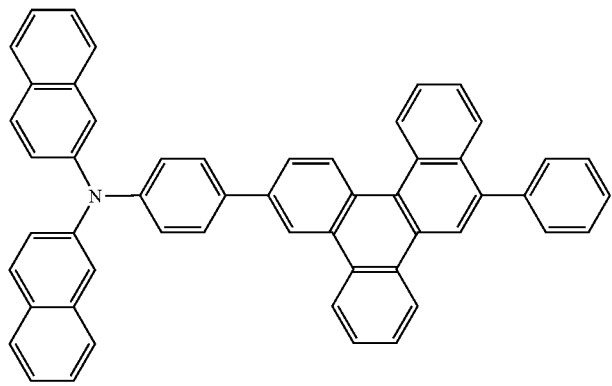

17

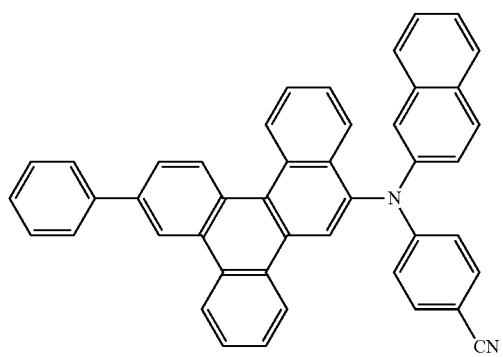

18

According to another aspect of the present invention, there is provided an organic light-emitting device including: a first electrode; a second electrode; and an organic layer disposed between the first electrode and the second electrode, wherein the organic layer may include a first layer including the compound of Formula 1 of claim 1.

In some embodiments the first layer may include an emission layer.

In some embodiments the first layer may include an emission layer, and the compound of Formula 1 may be used as a dopant.

In some embodiments the first layer may include an emission layer including the compound of Formula 1 as a dopant and a compound represented by Formula 2 as a host:

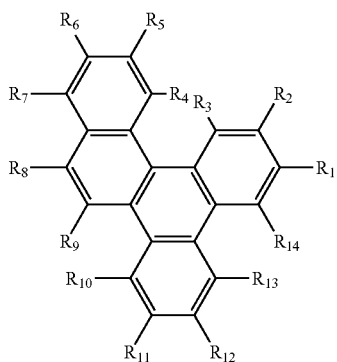

Formula 2 wherein in Formula 2, $R_1$ to $R_{14}$ may be each independently selected from the group consisting of a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted —$C_6$-$C_{60}$ aryloxy group, a substituted or unsubstituted $C_6$-$C_{60}$ arylthio group, a substituted or unsubstituted $C_6$-$C_{60}$ aryl group, a substituted or unsubstituted $C_4$-$C_{60}$ heteroaryl group, a substituted or unsubstituted $C_6$-$C_{60}$ condensed polycyclic group, a halogen atom, a cyano group, a nitro group, a hydroxyl group, and a carboxyl group; and $R_8$ and $R_9$ may be optionally linked together to form a saturated or unsaturated carbon ring.

In some embodiments $R_1$ to $R_{14}$ in Formula 2 may be each independently selected from the group consisting of a hydrogen atom, a deuterium atom, a cyano group, a halogen atom, a substituted or unsubstituted $C_1$-$C_{20}$ alkyl group, a substituted or unsubstituted $C_6$-$C_{40}$ aryl group, a substituted or unsubstituted $C_4$-$C_{40}$ heteroaryl group, and a substituted or unsubstituted $C_6$-$C_{40}$ condensed polycyclic group.

In some embodiments $R_1$ to $R_{14}$ in Formula 2 may be each independently selected from the group consisting of a hydrogen atom, a deuterium atom, a $C_1$-$C_{20}$ alkyl group, and groups represented by Formulae 4a to 4e below:

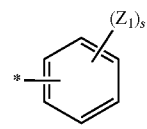

4a

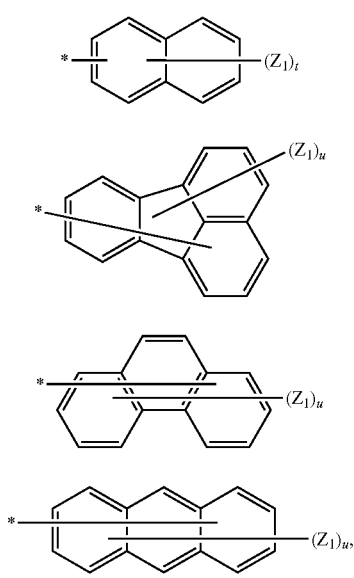

wherein in Formulae 4a to 4e, $Z_1$ may be selected from the group consisting of a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_4$-$C_{20}$ heteroaryl group, a substituted or unsubstituted $C_6$-$C_{20}$ condensed polycyclic group, a halogen atom, a cyano group, a nitro group, a hydroxyl group, and a carboxyl group;

s may be an integer from 1 to 5; t may be an integer from 1 to 7; u may be an integer from 1 to 9; and

* may indicate a binding site.

In some embodiments the compound of Formula 2 may include one of the compounds below:

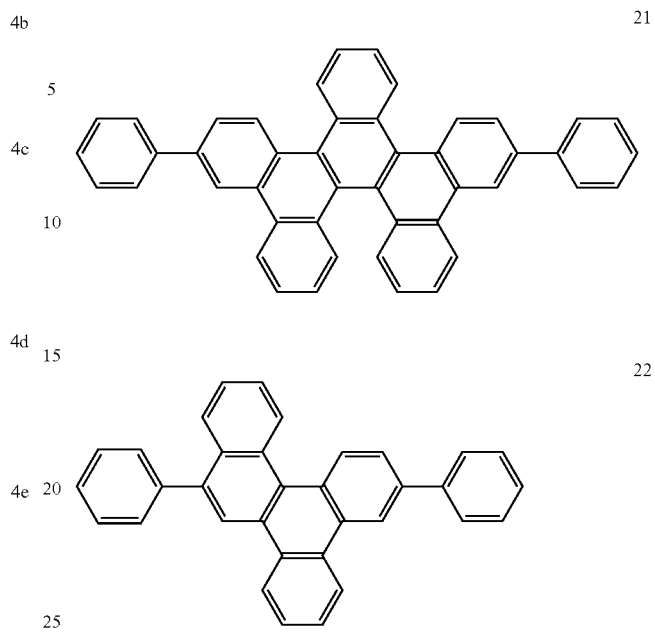

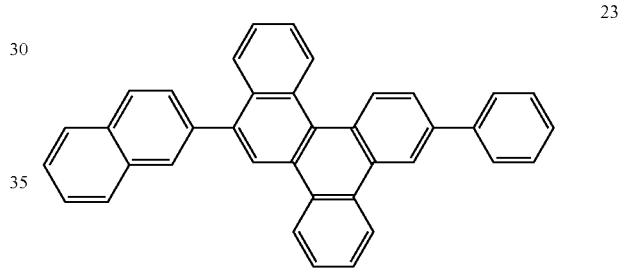

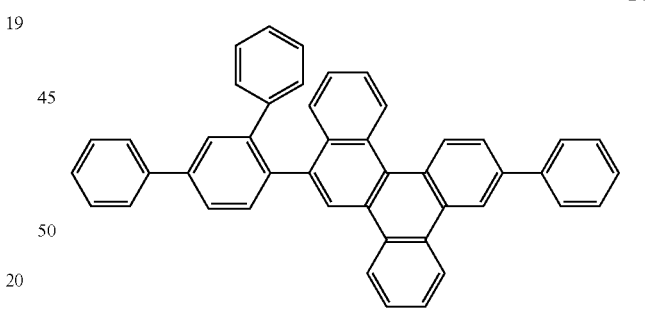

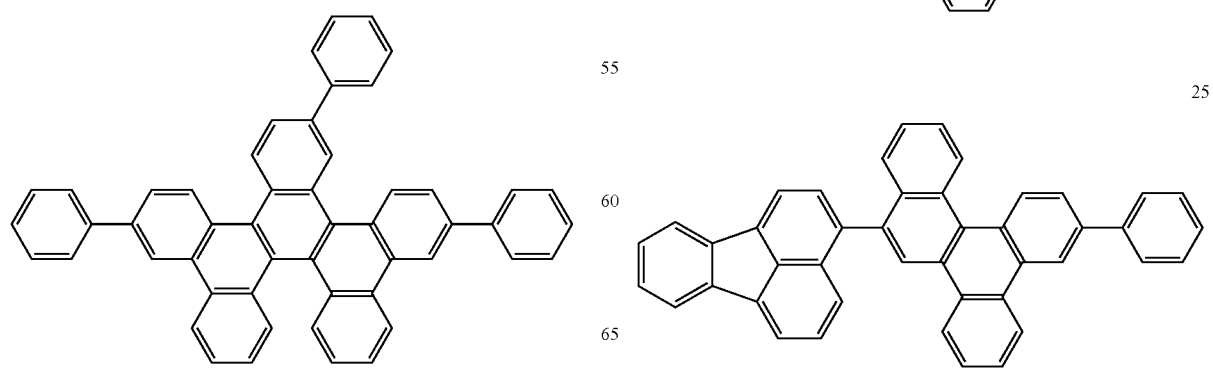

-continued

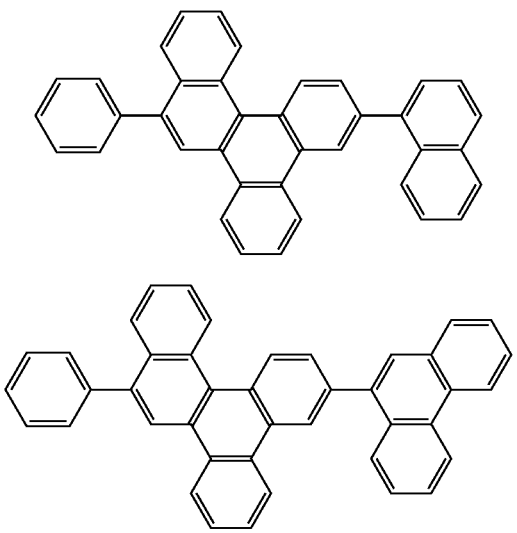

26

27

In some embodiments the emission layer may include a blue emission layer, the compound of Formula 1 may be used as a blue dopant, and the compound of Formula 2 may be used as a blue host.

In some embodiments the first layer may include an emission layer, and a red layer, a green layer, a blue layer, or a white layer of the emission layer may contain a phosphorescent compound.

In some embodiments the organic layer may further include a hole injection layer, a hole transport layer, a functional layer having both hole injection and hole transport capabilities, an emission layer, a hole blocking layer, an electron transport layer, an electron injection layer, or a combination of at least two thereof.

In some embodiments at least one of the hole injection layer, the hole transport layer, and the functional layer having hole injection and hole transport capabilities may further include a charge generating material.

In some embodiments the electron transport layer may include an electron transporting organic material and a metal-containing material. In some embodiments the metal-containing material may include a lithium (Li) complex.

BRIEF DESCRIPTION OF THE DRAWING

The above and other features and advantages of the present invention will become more apparent by describing in detail exemplary embodiments thereof with reference to the attached drawing in which:

FIG. 1 illustrates the structure of an organic light-emitting device according to an embodiment of the present invention.

DETAILED DESCRIPTION OF THE INVENTION

Anthracene derivatives are widely known as materials for an organic emission layer. Alq3, PBD, PF-6P, PyPySPyPy, and the like are known as electron transport materials. For example, an organic light-emitting device manufactured using a compound of phenylanthracene dimer or trimer is widely known. However, such organic light-emitting devices have a narrow energy gap and lower blue-light color purity since two or three oligomeric species of anthracene are linked by conjugation.

In addition, such compounds are highly vulnerable to oxidation and thus are liable to produce impurities, necessitating purification. In order to overcome these drawbacks, organic light-emitting devices manufactured using an anthracene compound including naphthalene substituted for anthracene at 1,9 positions or using a diphenylanthracene compound including an aryl group substituted for a phenyl group at m-position have been introduced. However, these organic light-emitting devices have a lower light-emission efficiency.

Organic light-emitting devices may also be manufactured using nathphalene-substituted monoanthracene derivatives. However, the light-emission efficiency thereof is low at about 1 cd/A, and thus such organic light-emitting devices are not suitable for practical use. Furthermore, organic light-emitting devices may be manufactured using phenylanthracene compounds including aryl substituents at m-position. Such a compound has excellent thermal resistance but leads to an unsatisfactorily low light-emission efficiency of about 2 cd/A.

The present invention will now be described more fully with reference to the accompanying drawings, in which exemplary embodiments of the invention are shown.

An aspect of the present invention provides a compound represented by Formula 1 below.

Formula 1

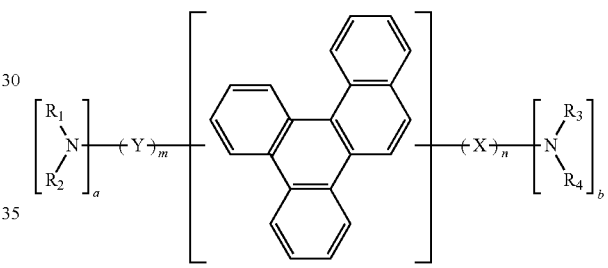

In Formula 1 above, X and Y are each independently a substituted or unsubstituted $C_6$-$C_{60}$ arylene group, a substituted or unsubstituted $C_4$-$C_{60}$ heteroarylene group, a substituted or unsubstituted $C_5$-$C_{60}$ cycloalkylene group, or a substituted or unsubstituted $C_5$-$C_{60}$ heterocycloalkylene group; and $R_1$ to $R_4$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ aryl group, a substituted or unsubstituted $C_4$-$C_{60}$ heteroaryl group, a substituted or unsubstituted $C_6$-$C_{60}$ condensed polycyclic group, a halogen atom, a cyano group, a nitro group, a hydroxyl group, or a carboxyl group;

In some embodiments, adjacent $R_1$ and $R_2$ or $R_3$ and $R_4$ may be linked together to form a saturated or unsaturated carbon ring; m and n may be independently an integer from 0 to 2; and a and b may be independently an integer from 0 to 2, but both a and b cannot be zero at the same time. Since a and b in Formula 1 are not both zero, the compound of Formula 1 may include at least one amine moiety.

In Formula 1, Y or X may be substituted at any position of benzochrysene. That is, Formula 1 shows that Y and X are bound to any position of bezochrysene. The compound of Formula 1 may be represented by Formula 1-1 below, which is a non-limiting example.

Formula 1-1

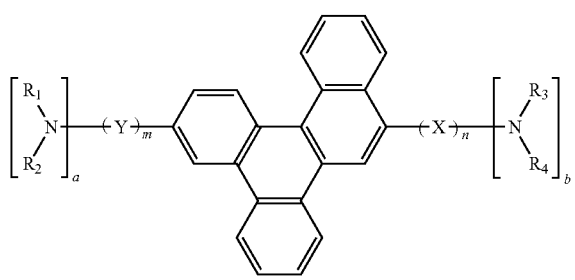

In some embodiments the compound of Formula 1 may be used in organic layers of organic light-emitting devices, for example, as a light-emitting material, a hole transporting material, or an electron transporting material of organic light-emitting devices. The compound of Formula 1 exhibits improved performance as a blue light-emitting material, and thus may be used as, for example, a deep blue material of a large-screen display having a non-resonant structure. In some embodiments the compound of Formula 1 may be used in a blue emission layer of an organic light-emitting device along with a compound of Formula 2, which will be described later. In some other embodiments, the compound of Formula 1 may be used as a dopant of a blue emission layer, while the compound of Formula 2 may be used as a host of the blue emission layer.

In some embodiments, X and Y in Formula 1 above may be each independently a substituted or unsubstituted $C_6$-$C_{30}$ arylene group, a substituted or unsubstituted $C_4$-$C_{20}$ heteroarylene group, a substituted or unsubstituted $C_5$-$C_{20}$ cycloalkylene group, or a substituted or unsubstituted $C_5$-$C_{20}$ heterocycloalkylene group; and $R_1$ to $R_4$ may be each independently a hydrogen atom, a deuterium atom, a cyano group, a halogen atom, a substituted or unsubstituted $C_1$-$C_{20}$ alkyl group, a substituted or unsubstituted $C_6$-$C_{40}$ aryl group, a substituted or unsubstituted $C_4$-$C_{40}$ heteroaryl group, or a substituted or unsubstituted $C_6$-$C_{40}$ condensed polycyclic group.

In some embodiments X and Y in Formula 1 may be each independently selected from groups represented by Formulae 2a to 2d below:

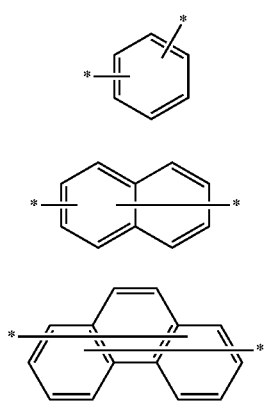

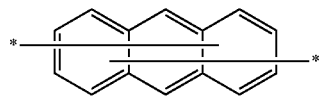

In Formulae 2a to 2d, * indicates a binding site.

In some embodiments $R_1$ to $R_4$ in Formula 1 may be each independently a hydrogen atom, a deuterium atom, a $C_1$-$C_{20}$ alkyl group, or groups represented by Formulae 3a to 3e below:

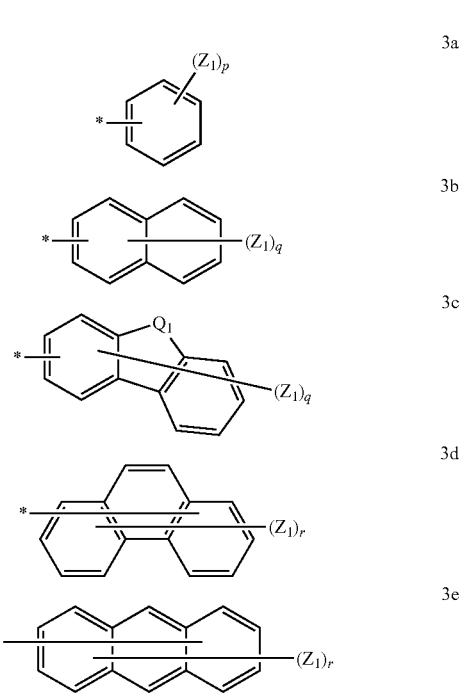

In Formulae 3a to 3e, $Q_1$ is a linking group represented by —C($R_5$)($R_6$)—, —N($R_7$)—, —S—, or —O—; $Z_1$, $R_5$, $R_6$, and $R_7$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_4$-$C_{20}$ heteroaryl group, a substituted or unsubstituted $C_6$-$C_{20}$ condensed polycyclic group, a halogen atom, a cyano group, a nitro group, a hydroxyl group, or a carboxyl group; p is an integer from 1 to 5; q is an integer from 1 to 7; r is an integer from 1 to 9; and * indicates a binding site.

According to an embodiment, an organic light-emitting device includes a first electrode, a second electrode, and an organic layer between the first electrode and the second electrode, the organic layer including the compound of Formula 1 described above.

In some embodiments the organic layer of the organic light-emitting device may be an emission layer, wherein the compound of Formula 1 above may be used as a dopant.

In some embodiments the organic layer of the organic light-emitting device may be an emission layer, wherein the compound of Formula 1 above may be used as a dopant, and a compound represented by Formula 2 below may be used a host.

Formula 2

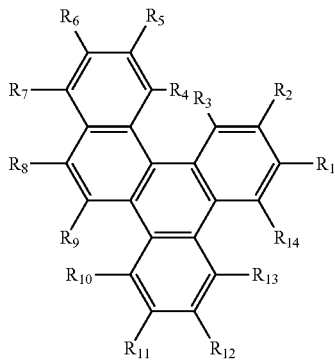

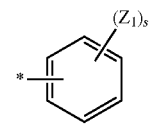
4a

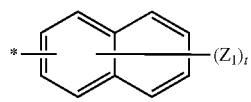
4b

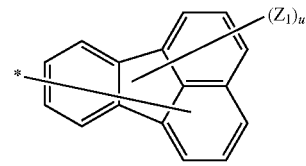
4c

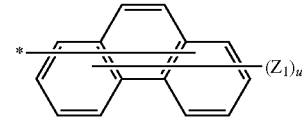
4d

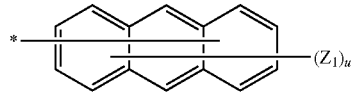
4e

In Formula 2, $R_1$ to $R_{14}$ are each independently a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ aryl group, a substituted or unsubstituted $C_4$-$C_{60}$ heteroaryl group, a substituted or unsubstituted $C_6$-$C_{60}$ condensed polycyclic group, a halogen atom, a cyano group, a nitro group, a hydroxyl group, or a carboxyl group. In some embodiments, $R_8$ and $R_9$ may be linked together to form a saturated or unsaturated carbon ring.

In some embodiments, $R_1$ to $R_{14}$ in Formula 2 above may be each independently a hydrogen atom, a deuterium atom, a cyano group, a halogen atom, a substituted or unsubstituted $C_1$-$C_{20}$ alkyl group, a substituted or unsubstituted $C_6$-$C_{40}$ aryl group, or a substituted or unsubstituted $C_4$-$C_{40}$ heteroaryl group, or a substituted or unsubstituted $C_6$-$C_{40}$ condensed polycyclic group.

In some embodiments $R_1$ to $R_{14}$ in Formula 2 may be each independently a hydrogen atom, a deuterium atom, a $C_1$-$C_{20}$ alkyl group, or groups represented by Formulae 4a to 4e below:

In Formulae 4a to 4e above, $Z_1$ is a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_4$-$C_{20}$ heteroaryl group, a substituted or unsubstituted $C_6$-$C_{20}$ condensed polycyclic group, a halogen atom, a cyano group, a nitro group, a hydroxyl group, or a carboxyl group; s is an integer of from 1 to 5; t is an integer from 1 to 7; u is an integer from 1 to 9; and * indicates a binding site.

In some embodiments, the organic layer may be a blue emission layer, wherein the compound of Formula 1 may be used as a blue dopant, and the compound of Formula 2 may be used as a blue host.

Examples of the compound represented by Formula 1 include compounds 1 to 18 below. However, the compounds represented by Formula 1 are not limited thereto.

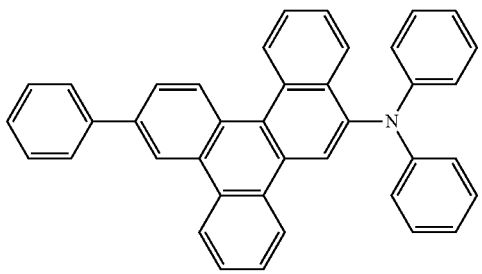

1

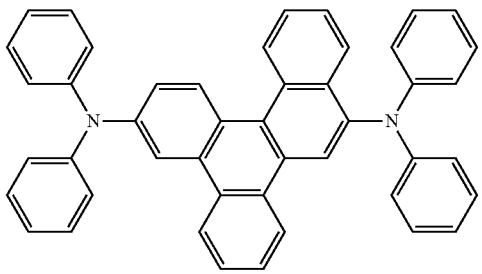

2

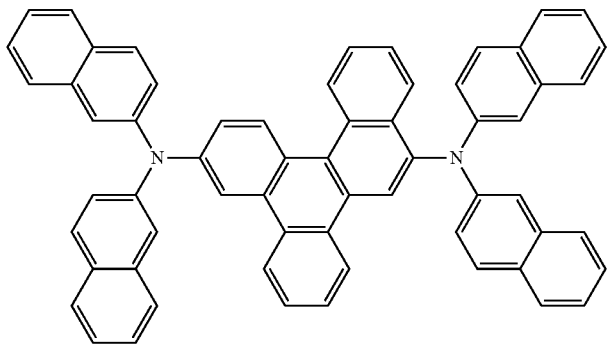
3
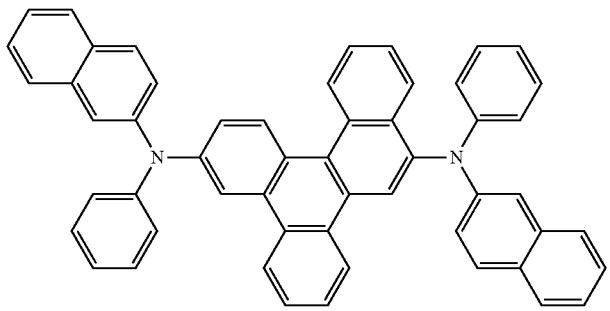
4
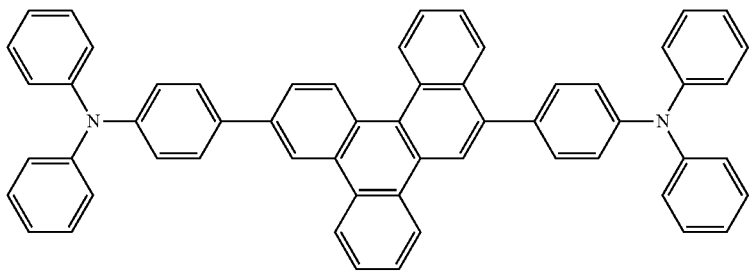
5
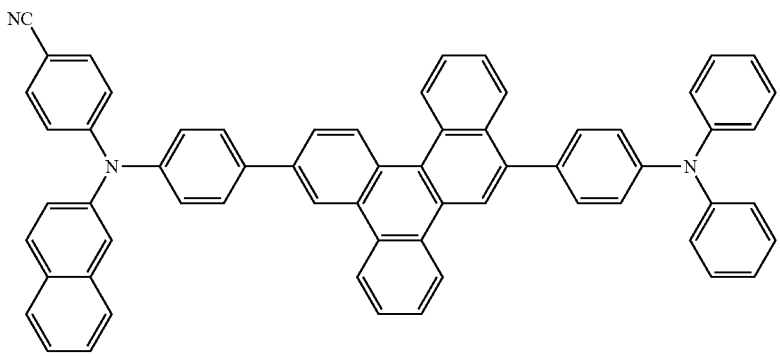
6
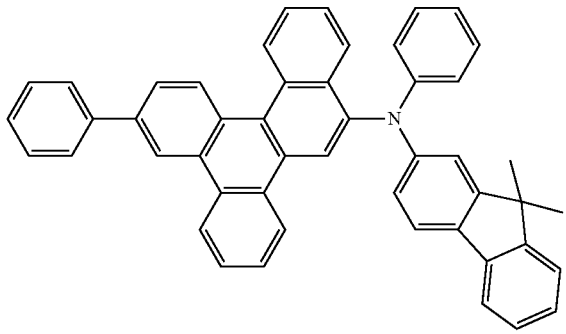
7

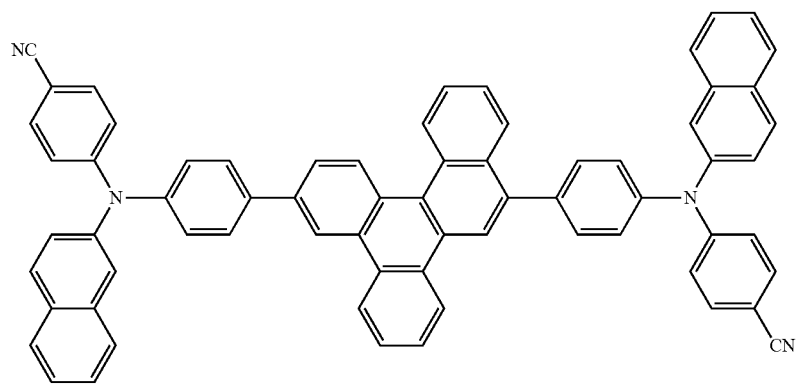
8
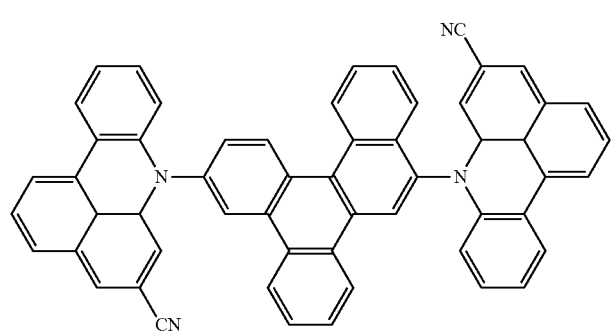
9
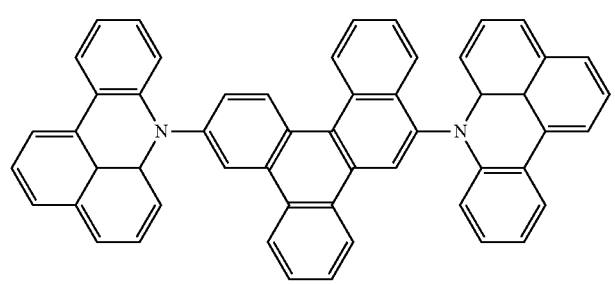
10
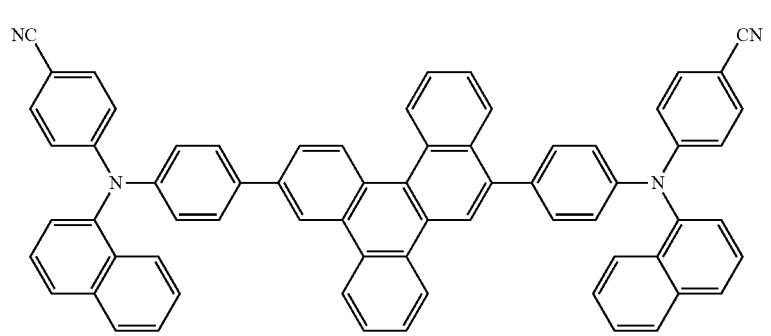
11
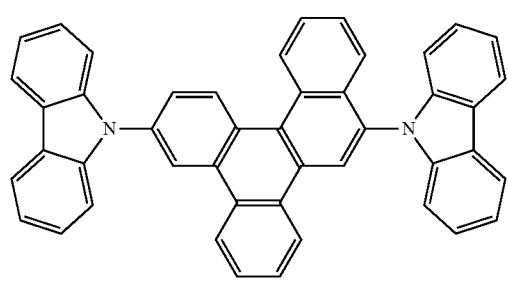
12

-continued
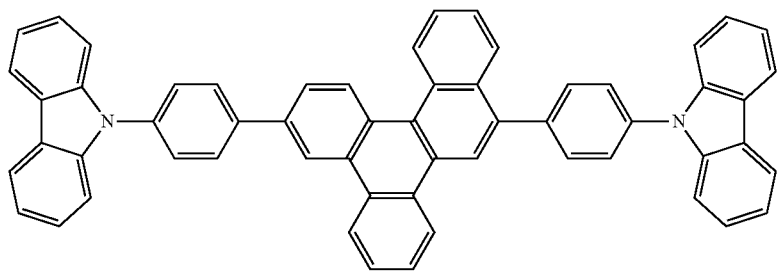
13
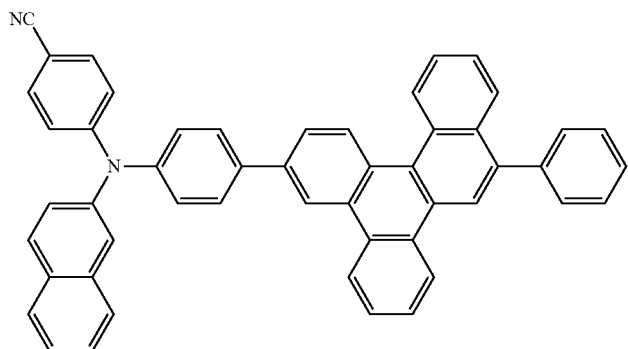
14
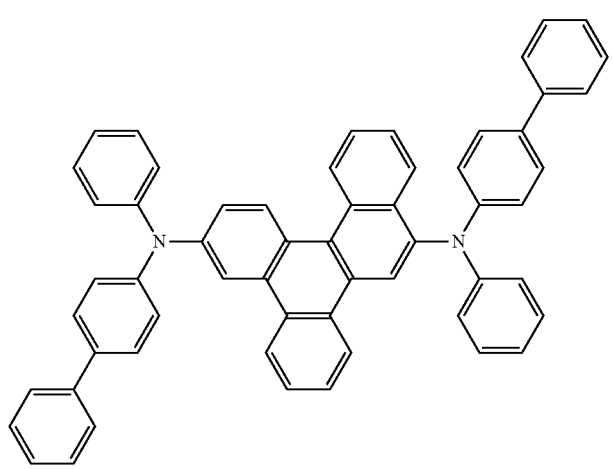
15
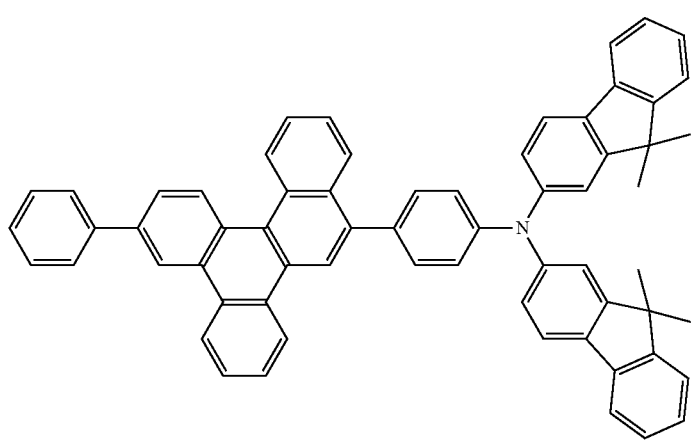
16

17
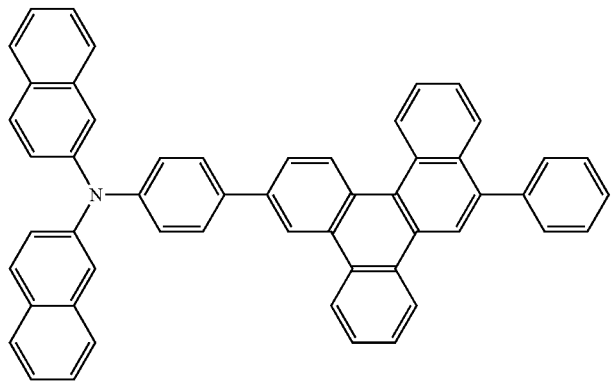
18
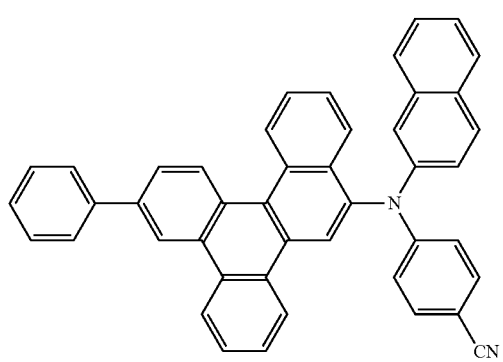
Examples of the compound represented by Formula 2 include compounds 19 to 27 below. However, the compounds represented by Formula 2 are not limited thereto.
19
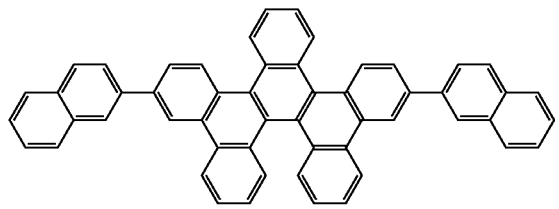
20
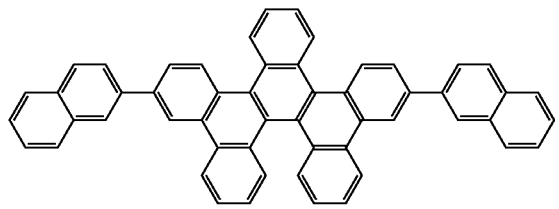
21
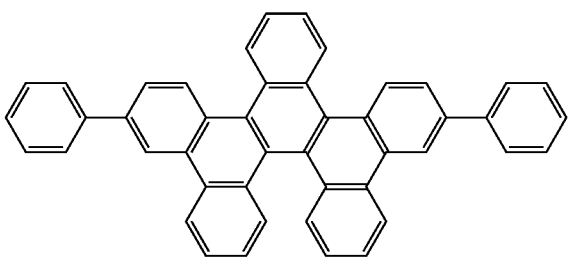
22
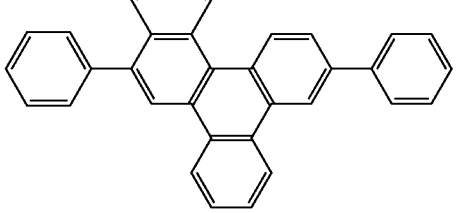
23
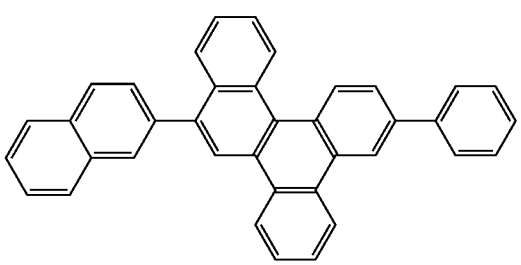

Hereinafter, substituents described with reference to Formulae 1 to 2 will now be described in detail. In this regard, the numbers of carbons in substituents are presented only for illustrative purposes and do not limit the characteristics of the substituents.

The unsubstituted $C_1$-$C_{60}$ alkyl group used herein may be linear or branched. Examples of the alkyl group include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group indicates an unsaturated alkyl group having at least one carbon-carbon double bond in the center (i.e. non-terminal) or at a terminal of the alkyl group. Examples of the alkenyl group include an ethenyl group, a propenyl group, a butenyl group, and the like. At least one hydrogen atom in the unsubstituted alkenyl group may be substituted with a substituent described above in conjunction with the alkyl group.

The unsubstituted $C_2$-$C_{60}$ alkynyl group indicates an alkyl group having at least one carbon-carbon triple bond in the center or at a terminal of the alkyl group. Examples of the unsubstituted $C_2$-$C_{20}$ alkynyl group include acetylene, propylene, phenylacetylene, naphthylacetylene, isopropylacetylene, t-butylacetylene, diphenylacetylene, and the like. At least one hydrogen atom in the alkynyl group may be substituted with a substituent described above in conjunction with the alkyl group.

The unsubstituted $C_3$-$C_{60}$ cycloalkyl group indicates a $C_3$-$C_{60}$ cyclic alkyl group wherein at least one hydrogen atom in the cycloalkyl group may be substituted with a substituent described above in conduction with the $C_1$-$C_{60}$ alkyl group.

The unsubstituted $C_1$-$C_{60}$ alkoxy group indicates a group having a structure of —OA wherein A is an unsubstituted $C_1$-$C_{60}$ alkyl group as described above. Non-limiting examples of the unsubstituted alkoxy group include a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted $C_6$-$C_{60}$ aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted $C_1$-$C_{60}$ alkyl group.

Examples of the substituted or unsubstituted $C_6$-$C_{60}$ aryl group include, but are not limited to, a phenyl group, a $C_1$-$C_{10}$ alkylphenyl group (for example, ethylphenyl group), a halophenyl group (for example, o-, m-, and p-fluorophenyl group, dichlorophenyl group), a cyanophenyl group, dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, a o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_4$-$C_{60}$ heteroaryl group used herein includes one, two or three hetero atoms selected from N, O, P and S. At least two rings may be fused to each other or linked to each other by a single bond. Examples of the unsubstituted $C_4$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted $C_1$-$C_{60}$ alkyl group.

The unsubstituted $C_5$-$C_{60}$ heterocycloalkyl group used herein includes one, two or three hetero atoms selected from N, O, P and S. At least two rings may be fused to each other or linked to each other by a single bond. In addition, at least one hydrogen atom in the heterocycloalkyl group may be substituted with a substituent described above in conjunction with the unsubstituted $C_1$-$C_{60}$ alkyl group.

The unsubstituted $C_6$-$C_{60}$ aryloxy group is a group represented by —$OA_1$ wherein $A_1$ may be a $C_6$-$C_{60}$ aryl group. An example of the aryloxy group is a phenoxy group. At least one hydrogen atom in the aryloxy group may be substituted with a substituent described above in conjunction with the unsubstituted $C_1$-$C_{60}$ alkyl group.

The unsubstituted $C_6$-$C_{60}$ arylthio group is represented by —$SA_1$ where $A_1$ may be a $C_6$-$C_{60}$ aryl group. Non-limiting examples of the arylthio group include a benzenethio group and a naphthylthio group. At least one hydrogen atom in the arylthio group may be substituted with a substituent described above in conjunction with the unsubstituted $C_1$-$C_{60}$ alkyl group.

The unsubstituted $C_6$-$C_{60}$ condensed polycyclic group used herein refers to a substituent including at least two rings wherein at least one aromatic ring and/or at least one non-aromatic ring are fused to each other.

The first electrode may be an anode, and the second electrode may be a cathode, but the reverse is also possible.

In some embodiments, the organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. In some other embodiments, the organic light-emitting device may have a first electrode/single layer having both hole injection and hole transport capabilities/emission layer/electron transport layer/second electrode structure, or a first electrode/single layer having both hole injection and hole transport capabilities/emission layer/electron transport layer/electron injection layer/second electrode structure. In some other embodiments, the organic light-emitting device may have a first electrode/hole transport layer/emission layer/single layer having both electron injection and electron transport capabilities/second electrode structure, a first electrode/hole injection layer/emission layer/single layer having both electron injection and electron transport capabilities/second electrode structure, or a first electrode/hole injection layer/hole transport layer/emission layer/single layer having both electron injection and electron transport capabilities/second electrode structure.

According to some embodiments of the present invention, the organic light-emitting device may have any of a variety of structures, for example, may be either a top-emission organic light-emitting device or a bottom-emission organic light-emitting device.

Hereinafter, a method of manufacturing an organic light-emitting device according to an embodiment of the present invention will be described with reference to FIG. 1. FIG. 1 illustrates the structure of an organic light-emitting device according to an embodiment of the present invention. Referring to FIG. 1, the organic light-emitting device according to an embodiment of the present embodiment includes a substrate (not shown), a first electrode (anode), a hole injection layer (HIL), a hole transport layer (HTL), an emission layer (EML), an electron transport layer (ETL), an electron injection layer (EIL), and a second electrode (cathode).

First, a first electrode is formed on a substrate by a deposition or sputtering method. The first electrode may be formed of a first electrode material having a high work function. The first electrode may constitute an anode or a cathode. The substrate may be a substrate conventionally used in organic light-emitting devices, and may include, for example, a glass substrate or a transparent plastic substrate with excellent mechanical strength, thermal stability, transparency, surface smoothness, ease of handling, and water resistance. Examples of the first electrode material include materials, such as indium tin oxide (ITO), indium zinc oxide (IZO), tin oxide ($SnO_2$), zinc oxide (ZnO), aluminum (Al), silver (Ag), and magnesium (Mg), which have excellent conductivity. The first electrode may be formed as a transparent or reflective electrode.

Next, the HIL may be formed on the first electrode using any of a variety of methods, for example, by vacuum deposition, spin coating, casting, Langmuir-Blodgett (LB) deposition, or the like.

When the HIL is formed using vacuum deposition, the deposition conditions may vary according to a material that is used to form the HIL, and the structure and thermal characteristics of the HIL. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, coating conditions may vary according to the material used to form the HIL, and the structure and thermal properties of the HIL. For example, the coating conditions may include a coating speed of about 2,000 rpm to about 5,000 rpm, and a thermal treatment temperature of about 80° C. to about 200° C. at which the solvent remaining after coating may be removed.

The HIL may be formed of the compound of Formula 1 or any material that is commonly used to form a HIL. Non-limiting examples of the material that can be used to form the HIL include a phthalocyanine compound such as copper-phthalocyanine, 4,4',4"-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

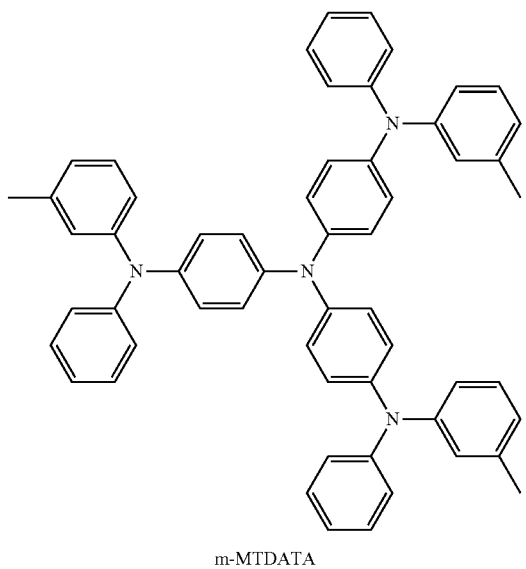

m-MTDATA

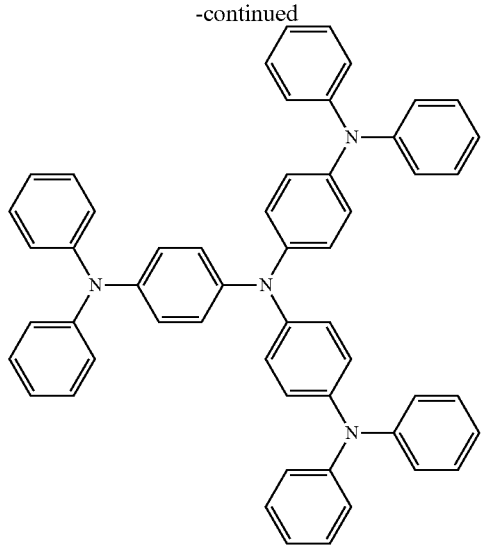

TDATA

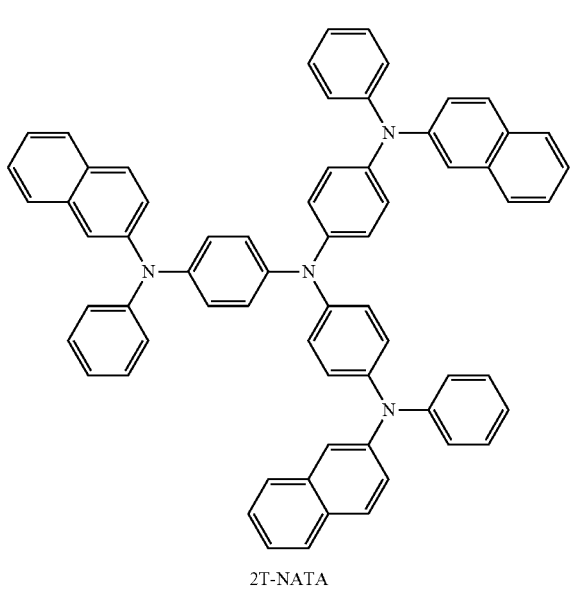

2T-NATA

The HIL may have a thickness of about 100 Å to about 10,000 Å, and in some other embodiments, may have a thickness of about 100 Å to about 1,000 Å. When the thickness of the HIL is within these ranges, the HIL may have good hole injection characteristics without an increase in driving voltage.

Next, the HTL may be formed on the HIL using any of a variety of methods, for example, vacuum deposition, spin coating, casting, LB deposition, or the like. When the HTL is formed using vacuum deposition or spin coating, the deposition or coating conditions may be similar to those applied to form the HIL, though the deposition or coating conditions may vary according to the material that is used to form the HTL.

The HTL may be formed of the compound of Formula 1 above or any known HTL material. Non-limiting examples of such HTL materials include carbazole derivatives such as N-phenylcarbazole or polyvinylcarbazole, and amine derivatives having an aromatic condensed ring, such as NPB, N,N'-bis(3-methylphenyl)-N,N'-diphenyl-[1,1-biphenyl]-4,4'-diamine (TPD), or the like.

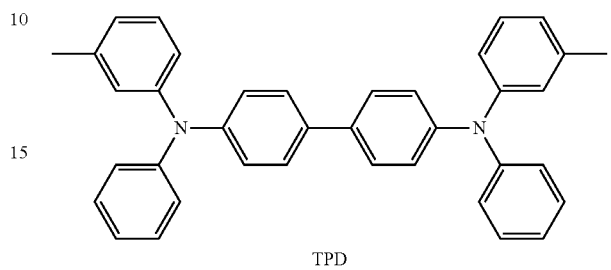

TPD

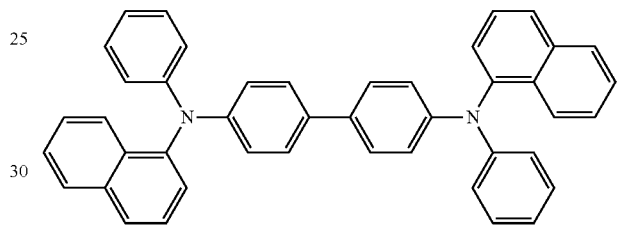

NPB

The HTL may have a thickness of about 50 Å to about 1,000 Å, and in some embodiments, may have a thickness of about 100 Å to about 600 Å. When the thickness of the HTL is within these ranges, the HTL may have good hole transport characteristics without a substantial increase in driving voltage.

Next, the EML may be formed on the HTL using any of a variety of methods, for example, by vacuum deposition, spin coating, casting, LB deposition, or the like. When the EML is formed using vacuum deposition or spin coating, the deposition or coating conditions may be similar to those applied to form the HIL, though the deposition or coating conditions may vary according to the material that is used to form the EML.

The EML may include the compound of Formula 1 or 2 described above. For example, the compound of Formula 1 or Formula 2 may be used as a host or a dopant. The EML may be formed using a variety of known light-emitting materials, in addition to the compound of Formula 1 or Formula 2. In some embodiments, the EML may also be formed using a known host and a dopant. Dopants that may be used to form the EML may include either a fluorescent dopant or a phosphorescent dopant which are widely known in the art.

Non-limiting examples of the host include Alq3, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, and distyrylarylene (DSA).

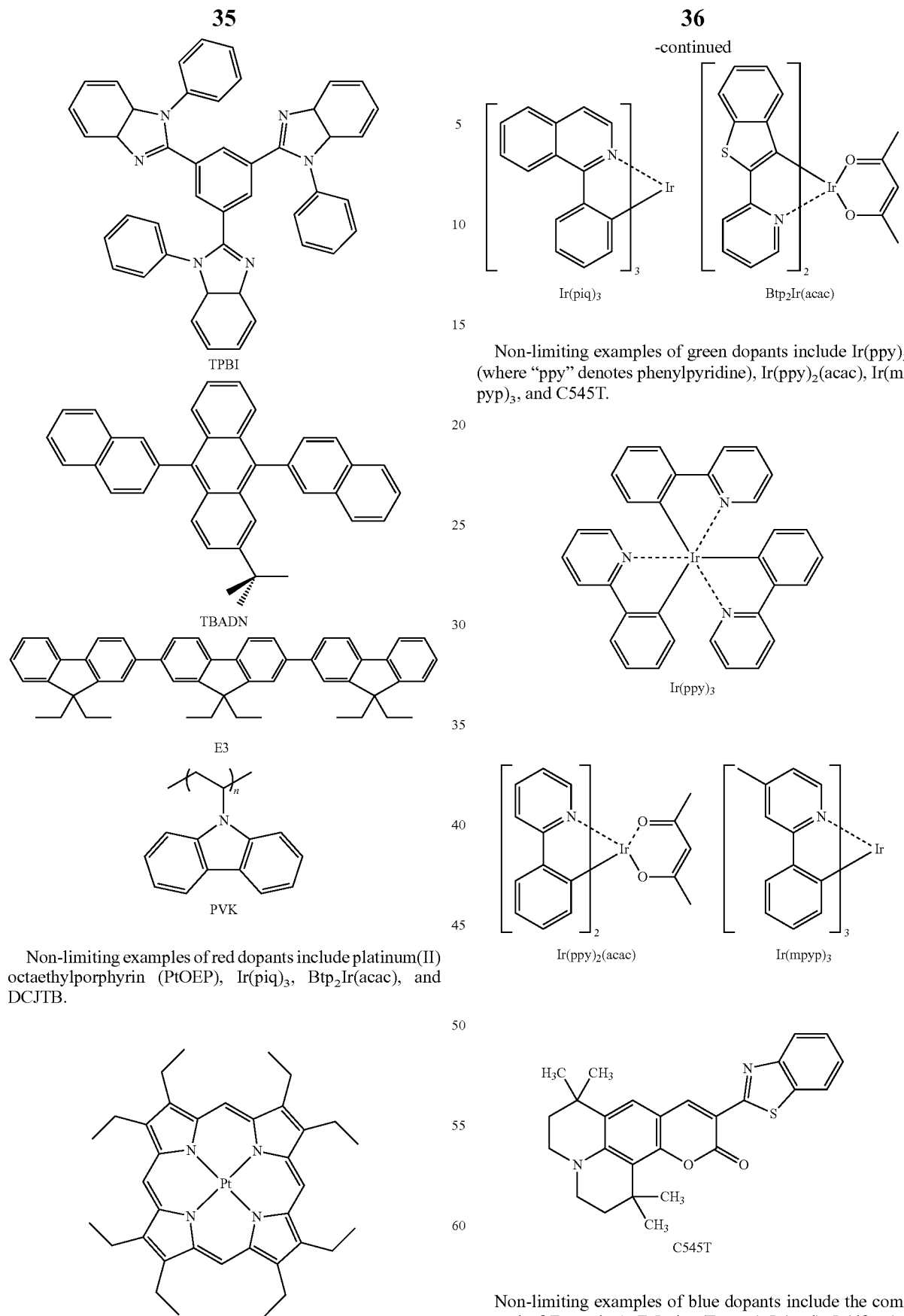

Non-limiting examples of green dopants include Ir(ppy)$_3$ (where "ppy" denotes phenylpyridine), Ir(ppy)$_2$(acac), Ir(m-pyp)$_3$, and C545T.

Non-limiting examples of red dopants include platinum(II) octaethylporphyrin (PtOEP), Ir(piq)$_3$, Btp$_2$Ir(acac), and DCJTB.

Non-limiting examples of blue dopants include the compound of Formula 1, F$_2$Irpic, (F$_2$ ppy)$_2$Ir(tmd), Ir(dfppz)$_3$, ter-fluorene, 4,4'-bis(4-diphenylaminostyryl)biphenyl (DPAVBi), and 2,5,8,11-tetra-t-butyl phenylene (TBP).

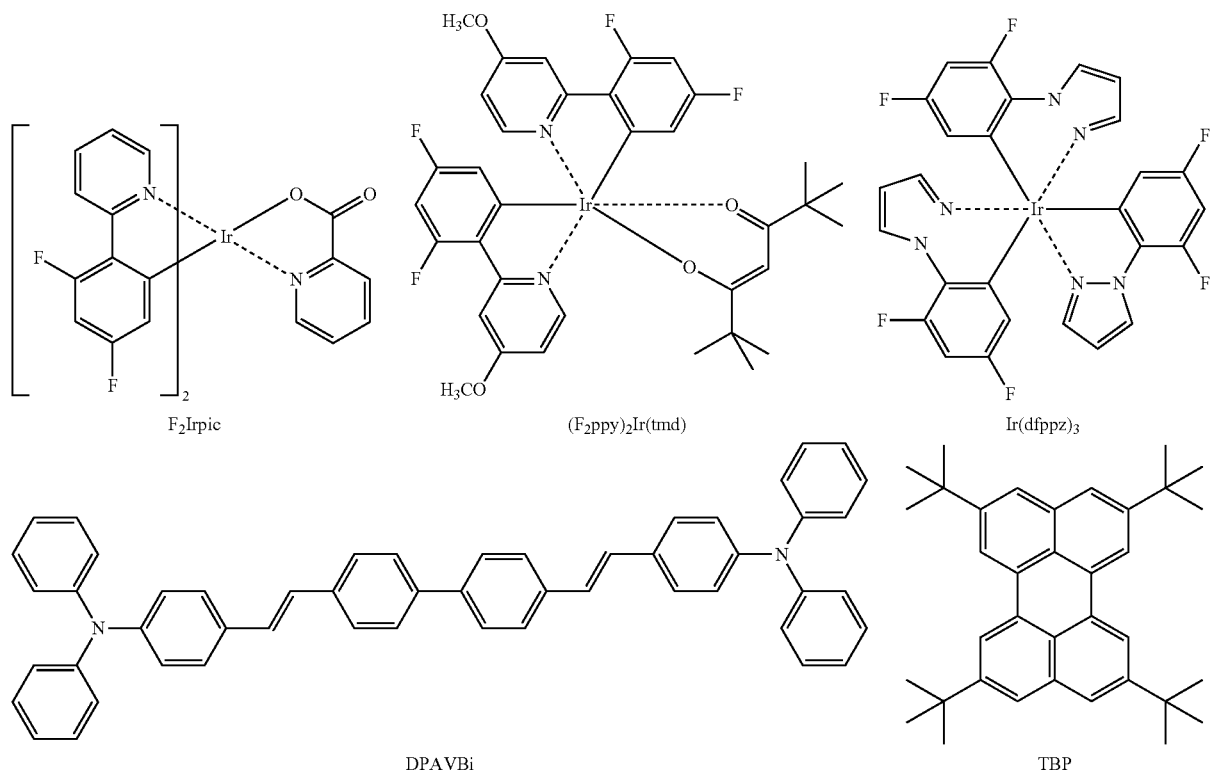

The amount of the dopant may be from about 0.1 to about 20 parts by weight, and in some other embodiments, may be from about 0.5 to about 12 parts by weight, based on 100 parts by weight of the EML material, which is equivalent to the total weight of the host and the dopant. When the amount of the dopant is within these ranges, concentration quenching may be substantially prevented.

The EML may have a thickness of about 100 Å to about 1,000 Å, and in some embodiments, may have a thickness of about 200 Å to about 600 Å. When the thickness of the EML is within these ranges, the EML may have good light-emitting characteristics without a substantial increase in driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may be formed of any material commonly used to form a HBL. Non-limiting examples of such HBL materials include oxadiazole derivatives, triazole derivatives, phenathroline derivatives, Balq, and BCP.

The HBL may have a thickness of about 50 Å to about 1,000 Å, and in some embodiments, may have a thickness of about 100 Å to about 300 Å. When the thickness of the HBL is within these ranges, diffusion of triplet exitons or holes into the ETL may be readily prevented without a substantial increase in driving voltage. Next, the ETL is formed on the EML (or HBL) using any of a variety of methods, for example, by vacuum deposition, spin coating, casting, or the like. When the ETL is formed using vacuum deposition or spin coating, the deposition or coating conditions may be similar to those applied to form the HIL, although the deposition or coating conditions may vary according to the material that is used to form the ETL.

The ETL may be formed of the compound of Formula 1 or any known materials used to form an ETL. Non-limiting examples of known electron transporting materials include quinoline derivatives, such as tris(8-quinolinorate)aluminum (Alq3), TAZ, BAlq, or the like.

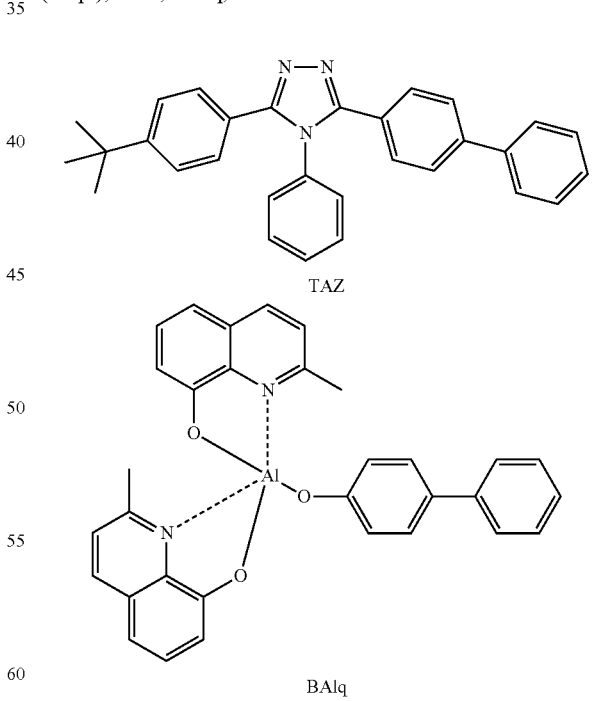

The ETL may have a thickness of about 100 Å to about 1,000 Å, and in some other embodiments, may have a thickness of about 100 Å to about 500 Å. When the thickness of the ETL is within these ranges, the ETL may have good electron transport characteristics without a substantial increase in driving voltage.

In addition, the EIL, which facilitates injection of electrons from the cathode, may be formed on the ETL.

The EIL may be formed of any known materials used to form an EIL layer, for example, LiF, NaCl, CsF, $Li_2O$, BaO, or the like. The deposition or coating conditions may be similar to those applied to form the HIL, although the deposition and coating conditions may vary according to the material that is used to form the EIL.

The EIL may have a thickness of about 1 Å to 100 Å, for example, about 5 Å to about 90 Å. When the thickness of the EIL is within these ranges, the EIL may have good electron injection characteristics without a substantial increase in driving voltage.

Finally, the second electrode may be formed on the EIL by, for example, vacuum deposition, sputtering, or the like. The second electrode may constitute a cathode or an anode. The material for forming the second electrode may include a metal, an alloy, or an electrically conductive compound, which are materials having a low work function, or a mixture thereof. Non-limiting examples of such materials include lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission organic light-emitting device, a transparent cathode formed of a transparent material such as ITO or IZO may be used as the second electrode.

In some embodiments an emission layer of the organic light-emitting device, i.e., a red, green, blue, or white emission layer, may further include a widely-known phosphorescent compound.

In some embodiments, the organic layer of the organic light-emitting device may further include, but are not limited to, a hole injection layer, a hole transport layer, a functional layer having both hole injection and hole transport capabilities, an emission layer, a hole blocking layer, an electron transport layer, an electron injection layer, or a combination of at least two thereof. At least one of the hole injection layer, the hole transport layer and the functional layer having both hole injection and hole transport capabilities may further include a charge generating material for improved layer conductivity, in addition to the compound of Formula 1 or 2 described above, a widely-known hole injection material, and a widely-known hole transport material.

The charge generating material may include, for example, a p-dopant. Non-limiting examples of the p-dopant include quinone derivatives such as tetracyanoquinonedimethane (TCNQ), 2,3,5,6-tetrafluoro-tetracyano-1,4-benzoquinonedimethane (F4TCNQ), and the like; metal oxides such as tungsten oxide, molybdenum oxide, and the like; and cyano-containing compounds such as Compound 100 below.

Compound 100

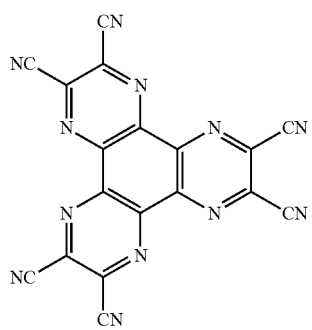

When the hole injection layer, the hole transport layer, or the functional layer having both hole injection and hole transport capabilities further includes a charge generating material, the charge generating material may be, but not limited to, uniformly dispersed or nonuniformly distributed in the layer.

In some embodiments the electron transport layer of the organic light-emitting device may further include an electron-transporting organic compound and a metal-containing material. Non-limiting examples of the electron-transporting organic compound include 9,10-di(naphthalen-2-yl)anthracene (ADN), and anthracene-based compounds, such as Compounds 101 and 102 below.

Compound 101

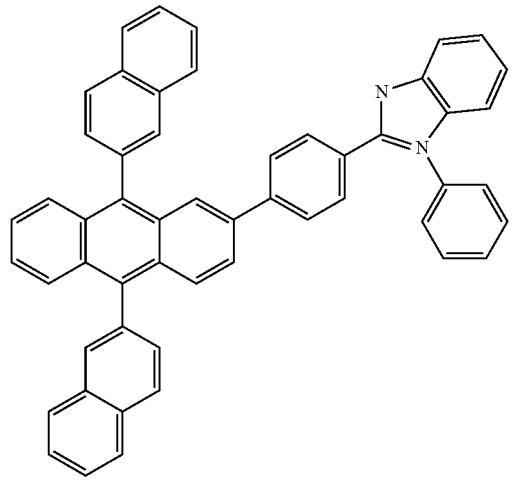

Compound 102

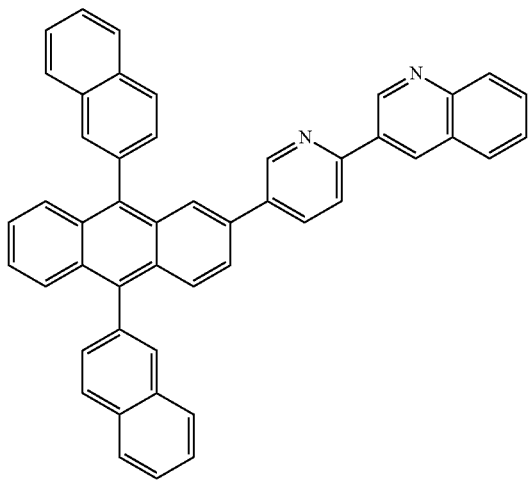

The metal-containing material may include a lithium (Li) complex. Non-limiting examples of the Li complex include lithium quinolate (LiQ), Compound 103 below, and the like:

Compound 103

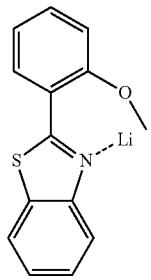

According to embodiments of the present invention, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

Hereinafter, synthesis examples of Compounds 2, 13, 15, and 22 and examples will be described in detail. However, these examples are for illustrative purposes only, and are not intended to limit the scope of the present invention.

EXAMPLES

Synthesis Example 1

Synthesis of Intermediate 1

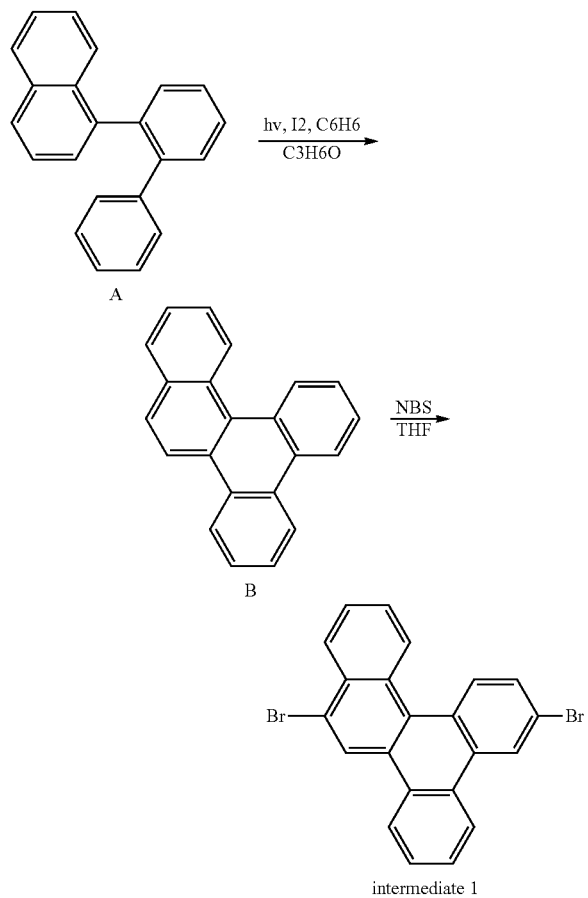

4.74 g of Compound A, 3.30 g of iodine, and 40 mL of propylene oxide were placed into a quartz flask filled with 550 mL of benzene and nitrogen, and were reacted for about 12 hours with an irradiation of 450-W medium-pressure mercury UV-lamp. After the reaction was completed, a reaction product was recrystallized with a benzene/hexane solution to obtain an intermediate B (Yield: 90%). The Intermediate B and NBS were dissolved in THF in a round flask with an agitation for about 1 hour, and then 100 ml of water was added to terminate the reaction, followed by an extraction to obtain white solid Intermediate 1 (Yield: 70%).

Synthesis Example 2

Synthesis of Compound 2

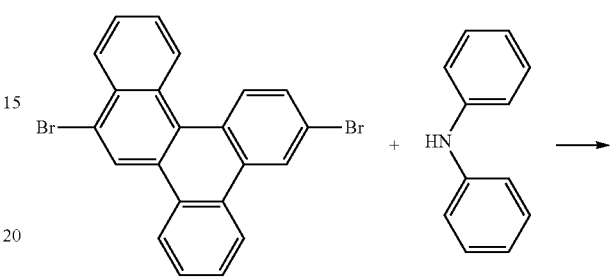

1 mmol of Intermediate 1, 1 mmol of diphenyl amine, 1.5 mmol of t-BuONa, 0.02 mmol of $Pd_2(dba)_3$, and 0.01 mmol of $P(t-Bu)_3$ were dissolved in 5 mL of toluene, and the mixture was stirred at about 90° C. for about 3 hours. After the reaction was completed, the reaction product was cooled to room temperature and extracted three times with distilled water and 30 ml of diethylether. The organic phase was collected, and was dried using magnesium sulfate until the solvent evaporated. The residue was separated and purified using silica gel column chromatography to obtain Compound 2 (Yield: 70%).

Synthesis Example 3

Synthesis of Compound 22

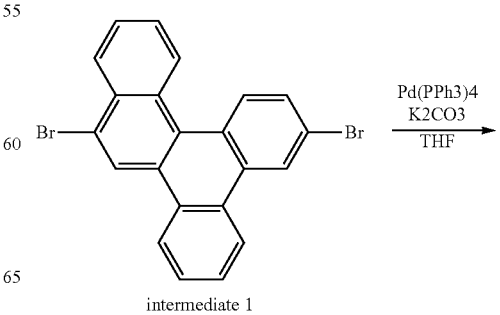

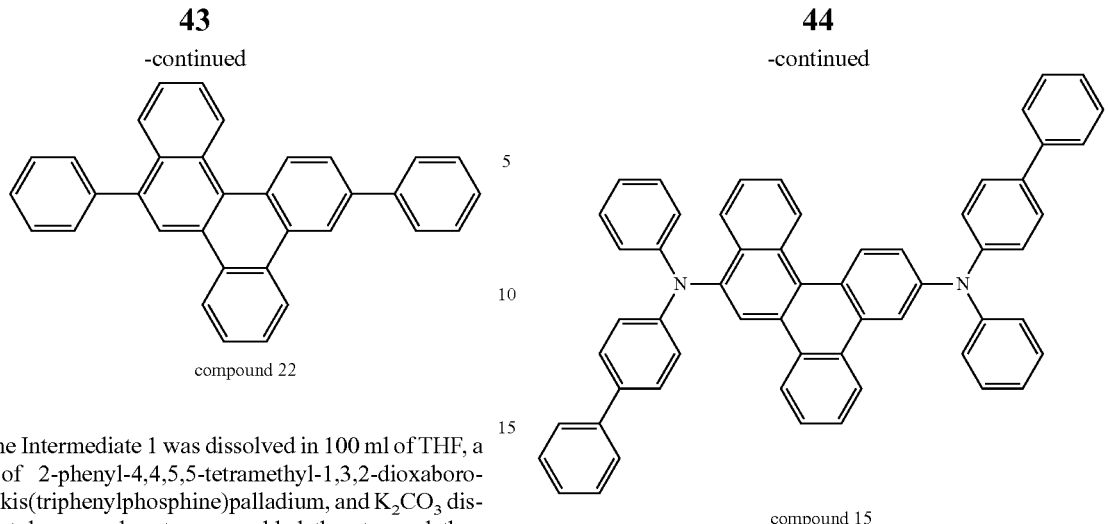

compound 22

After the Intermediate 1 was dissolved in 100 ml of THF, a solution of 2-phenyl-4,4,5,5-tetramethyl-1,3,2-dioxaborolane, tetrakis(triphenylphosphine)palladium, and $K_2CO_3$ dissolved in toluene and water was added thereto, and then refluxed for about 12 hours with an agitation. After the reaction product was cooled to room temperature, 100 ml of diethylether was added thereto, and the mixture was washed twice with 100 ml of water to collect the organic phase, which was then dried over anhydrous magnesium sulfate. The remaining solvent was evaporated to obtain a crude product, followed by an isolation and purification using silica gel column chromatography and by recrystallization to obtain Compound 22 with a yield of 85%.

Synthesis Example 4

Synthesis of Compound 15

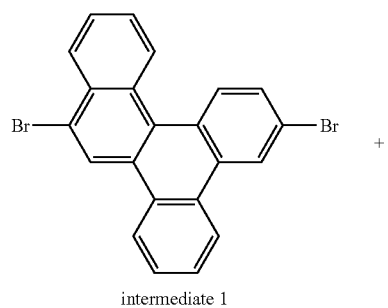

intermediate 1

+ intermediate 4 compound 15

Compound 15 was synthesized in the same manner as in Synthesis Example 2, except that N-phenyl-4-biphenylamine was used instead of diphenylamine.

Synthesis Example 5

Synthesis of Compound 13

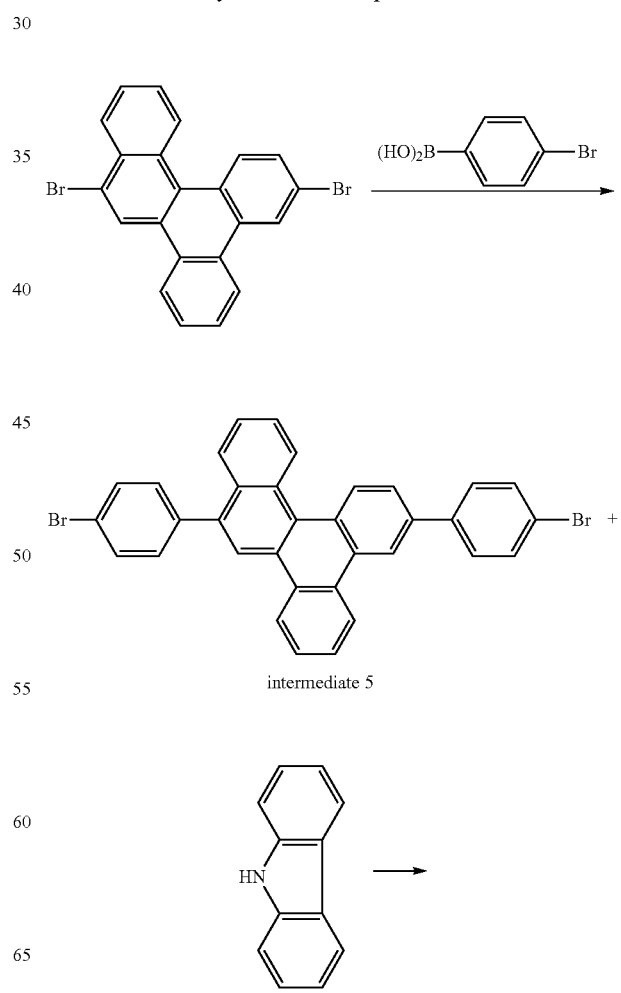

intermediate 5

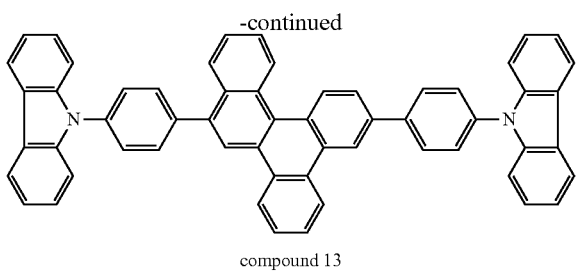

compound 13

Compound 13 was synthesized in the same manner as in Synthesis Examples 2 and 4, in which the synthesized Intermediate 5 was reacted with carbazole.

Example 1

As an anode, an ITO glass substrate (1000 Å) was cut to a size of 50 mm×50 mm×0.7 mm, ultrasonically washed with isopropyl alcohol and pure water for about 15 minutes each, and then washed with UV ozone for about 10 minutes. By using the synthesized Compound 2 as a dopant of an emission layer and TBADN as a host, an organic light-emitting device having the following structure was manufactured: ITO (1000 Å)/(M-TDATA) (35 nm)/α-NPD (30 nm)/95 wt % of TBADN compound/5 wt % of Compound 2 (35 nm)/Alq3 (18 nm)/LiF (0.7 nm)/Al (150 nm).

M-TDATA was vacuum-deposited to a thickness of about 35 nm, and α-NPD was then vacuum-deposited thereon to a thickness of about 30 nm. Afterward, TBADN and Compound 2 were vacuum-deposited in a 95:5 ratio by weight to a thickness of about 35 nm, thereby forming an emission layer. Then, Alq3 was vacuum-deposited on the emission layer to a thickness of 18 nm to form an electron transport layer. LiF was vacuum-deposited on the electron transport layer to a thickness of 0.7 nm to form an electron injection layer, and Al was then vacuum-deposited to a thickness of 150 nm on the electron injection layer to form a cathode, thereby manufacturing an organic light-emitting device.

Example 2

By using the synthesized Compound 15 as a dopant of an emission layer and TBADN as a host, an organic light-emitting device having the following structure was manufactured: ITO (1000 Å)/(M-TDATA) (35 nm)/α-NPD (30 nm)/95 wt % of TBADN compound/5 wt % of Compound 15 (35 nm)/Alq3 (18 nm)/LiF (0.7 nm)/Al (150 nm).

An organic light-emitting device was manufactured in the same manner as in Example 1.

Example 3

As an anode, an ITO glass substrate (1000 Å) was cut to a size of 50 mm×50 mm×0.7 mm, ultrasonically washed with isopropyl alcohol and pure water for about 15 minutes each, and then washed with UV ozone for about 10 minutes. By using the synthesized Compound 22 as a host of an emission layer and the Compound 2 as a dopant, an organic light-emitting device having the following structure was manufactured: ITO (1000 Å)/(M-TDATA) (35 nm)/α-NPD (30 nm)/95 wt % of Compound 22/5 wt % of Compound 2 (35 nm)/Alq3 (18 nm)/LiF (0.7 nm)/Al (150 nm).

An organic light-emitting device was manufactured in the same manner as in Example 1.

Comparative Example 1

An organic light-emitting device was manufactured in the same manner as in Example 1, except that only DPAVBi was used as an emission material instead of the synthesized compound of Formula 2. Emission characteristics of the organic light-emitting device are presented in Table 1.

TABLE 1

| | Driving voltage (V) @1,000 nit | Maximum current efficiency (cd/A) | CIE color coordinates (~1,000 cd/m$^2$) |
|---|---|---|---|
| Comparative Example 1 | 4.5 | 8.9 | (0.15, 0.230) |
| Example 1 | 4.2 | 4.2 | (0.14, 0.084) |
| Example 2 | 4.2 | 4.5 | (0.15, 0.092) |
| Example 3 | 4.2 | 4.1 | (0.14, 0.079) |

The organic light-emitting devices of Examples 1-3, which were manufactured using a compound according to an embodiment of the present invention as a dopant (Examples 1 and 2) or using compounds according to an embodiment of the present invention as a host and dopant (Example 3), are found having deeper blue color coordinates, a reduced driving voltage, and a higher efficiency by about 20% or greater with respect to relative color coordinates, as compared to the organic light-emitting device of Comparative Example 1.

According to the one or more embodiments, due to having improved emission efficiency and color purity, a compound may be used, for example, as an emission material suitable for blue-light emitting devices, and thus may be suitable for large-screen displays, in particular, as a deep blue material.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. A compound represented by Formula 1 below:

[Formula 1]

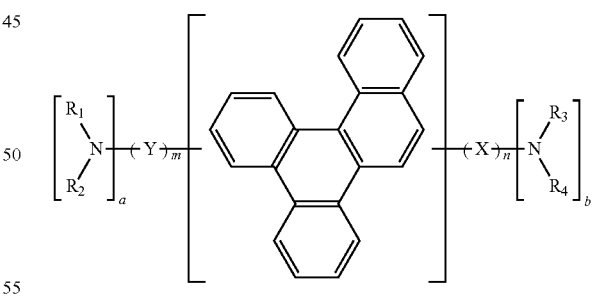

X and Y in Formula 1 are each independently selected from the group consisting of a substituted or unsubstituted $C_6$-$C_{60}$ arylene group, a substituted or unsubstituted $C_4$-$C_{60}$ heteroarylene group, a substituted or unsubstituted $C_5$-$C_{60}$ cycloalkylene group, and a substituted or unsubstituted $C_5$-$C_{60}$ heterocycloalkylene group;
$R_1$ to $R_4$ are each independently selected from the group consisting of a hydrogen atom, a deuterium atom, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{60}$ cycloalkyl group, a substituted or unsubstituted $C_1$-$C_{60}$ alkoxy group, a substituted or unsubstituted $C_6$-$C_{60}$ aryloxy group, a substituted or unsubstituted $C_6$-$C_{60}$ arylthio group, a substituted or unsubstituted $C_6$-$C_{60}$ aryl group, a substituted or unsubstituted $C_4$-$C_{60}$ heteroaryl group, a substituted or unsubstituted $C_6$-$C_{60}$ condensed polycyclic group, a halogen atom, a cyano group, a nitro group, a hydroxyl group, and a carboxyl group;

adjacent $R_1$ and $R_2$ or $R_3$ and $R_4$ are optionally linked together to form a saturated or unsaturated carbon ring;

m and n are each independently an integer from 0 to 2; and a and b are each independently an integer from 0 to 2 with a proviso that both a and b are not zero at the same time.

2. The compound of claim 1, X and Y in Formula 1 are each independently selected from the group consisting of a substituted or unsubstituted $C_6$-$C_{30}$ arylene group, a substituted or unsubstituted $C_4$-$C_{20}$ heteroarylene group, a substituted or unsubstituted $C_5$-$C_{20}$ cycloalkylene group, and a substituted or unsubstituted $C_5$-$C_{20}$ heterocycloalkylene group; and $R_1$ to $R_4$ are each independently selected from the group consisting of a hydrogen atom, a deuterium atom, a cyano group, a halogen atom, a substituted or unsubstituted $C_1$-$C_{20}$ alkyl group, a substituted or unsubstituted $C_6$-$C_{40}$ aryl group, a substituted or unsubstituted $C_4$-$C_{40}$ heteroaryl group, and a substituted or unsubstituted $C_6$-$C_{40}$ condensed polycyclic group.

3. The compound of claim 1, wherein X and Y in Formula 1 are each independently selected from groups represented by Formulae 2a to 2d below:

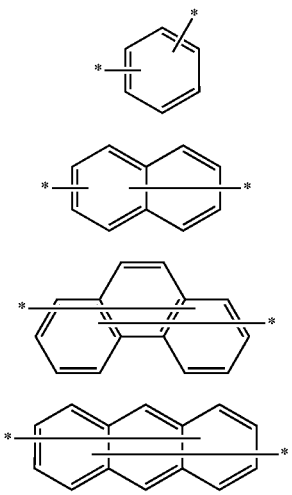

wherein in Formulae 2a to 3d, * indicates a binding site.

4. The compound of claim 1, $R_1$ to $R_4$ in Formula 1 are each independently selected from the group consisting of a hydrogen atom, a deuterium atom, a $C_1$-$C_{20}$ alkyl group, and groups represented by Formulae 3a to 3e below:

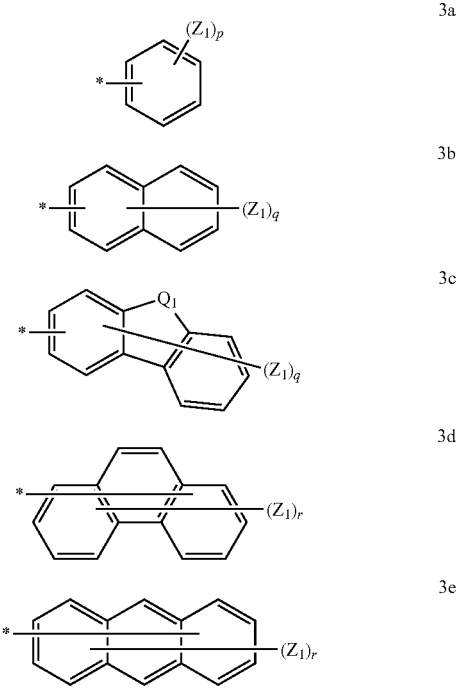

$Q_1$ in Formulae 3a to 3e is a linking group represented by —C($R_5$)($R_6$)—, —N($R_7$)—, —S—, or —O—;

$Z_1$, $R_5$, $R_6$, and $R_7$ are each independently selected from the group consisting of a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_4$-$C_{20}$ heteroaryl group, a substituted or unsubstituted $C_6$-$C_{20}$ condensed polycyclic group, a halogen atom, a cyano group, a nitro group, a hydroxyl group, and a carboxyl group;

p is an integer from 1 to 5;

q is an integer from 1 to 7;

r is an integer from 1 to 9; and

* indicates a binding site.

5. The compound of claim 1, wherein the compound of Formula 1 comprises one of the compounds below:

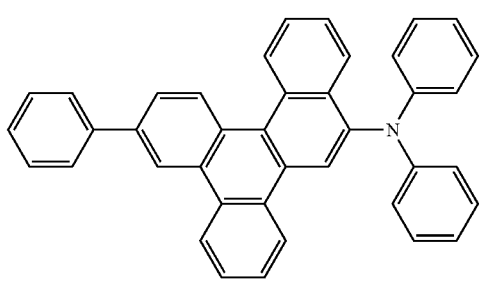

1

-continued
2
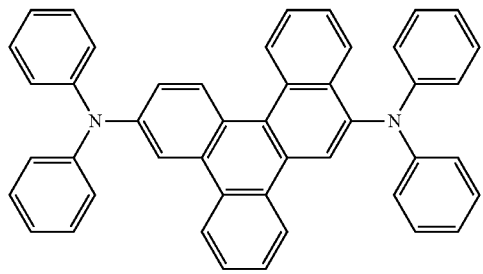
3
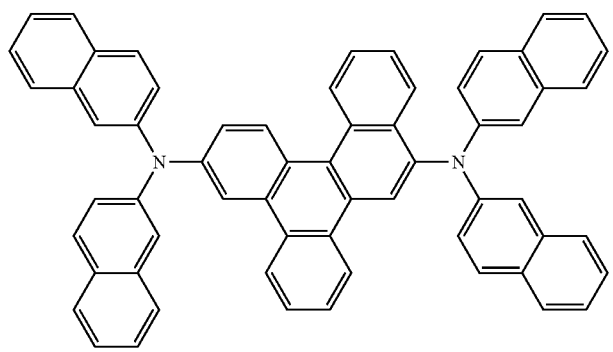
4
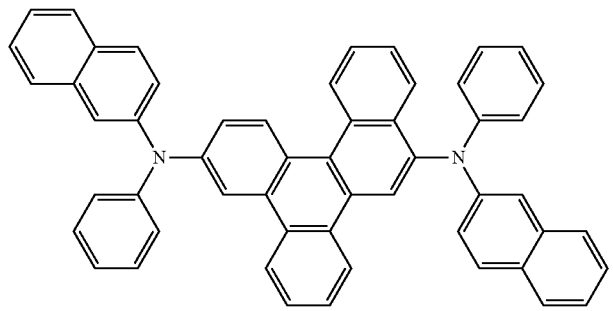
5
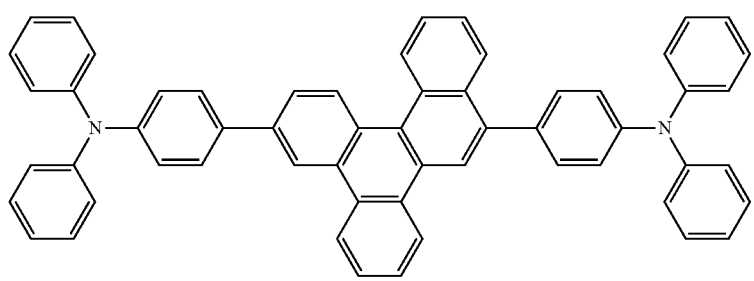
6
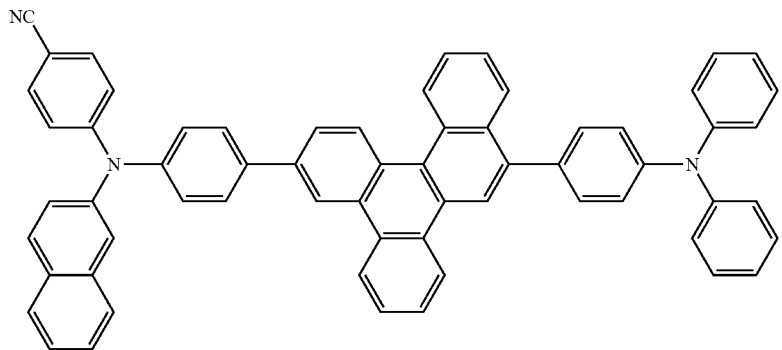

7
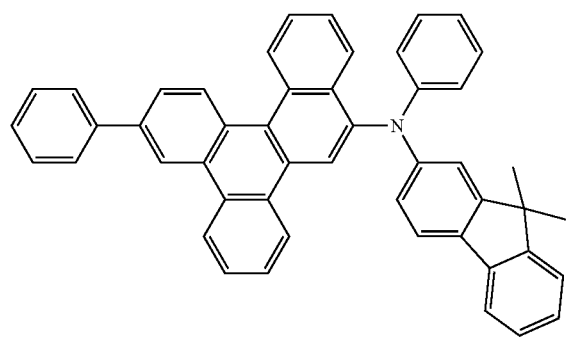
8
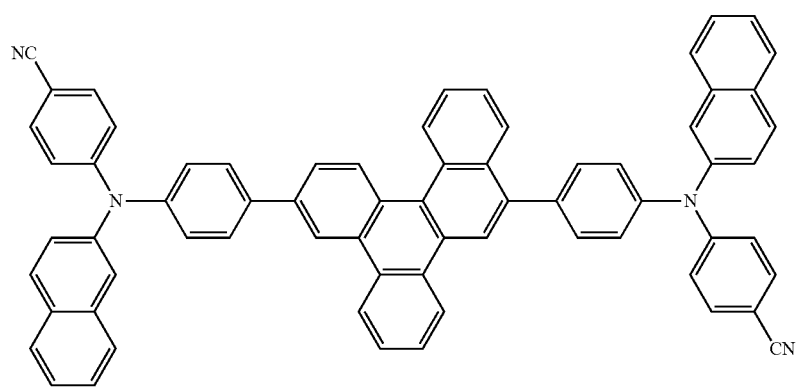
9
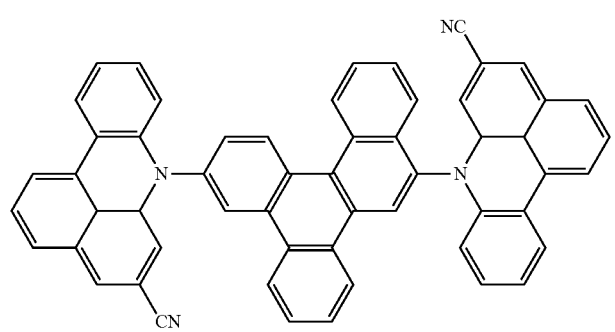
10
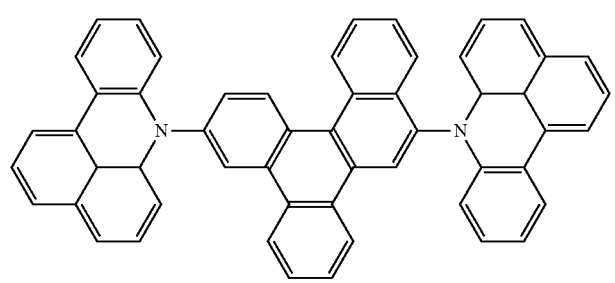
11
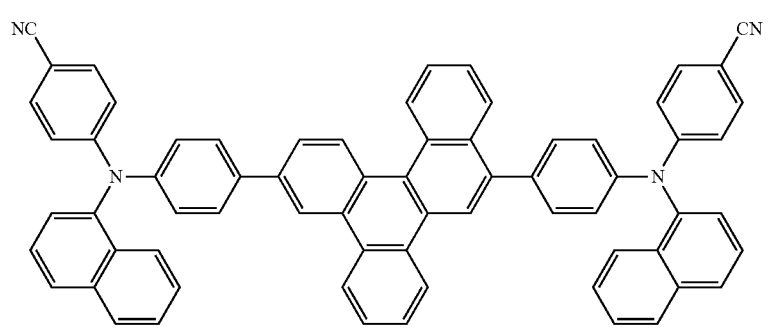

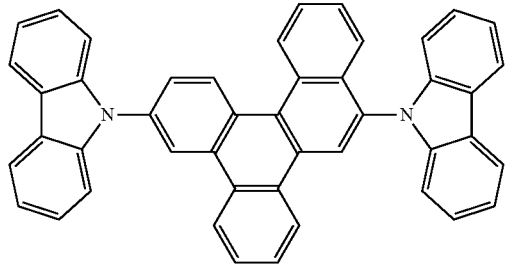
12
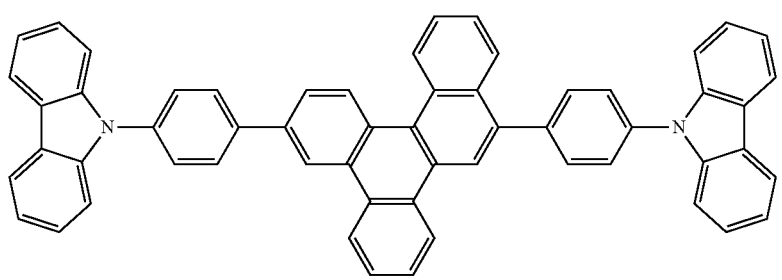
13
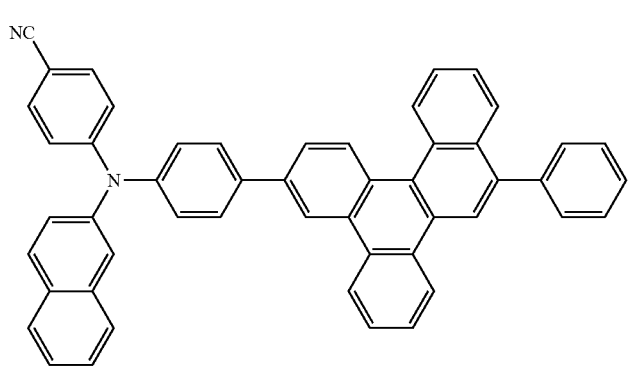
14
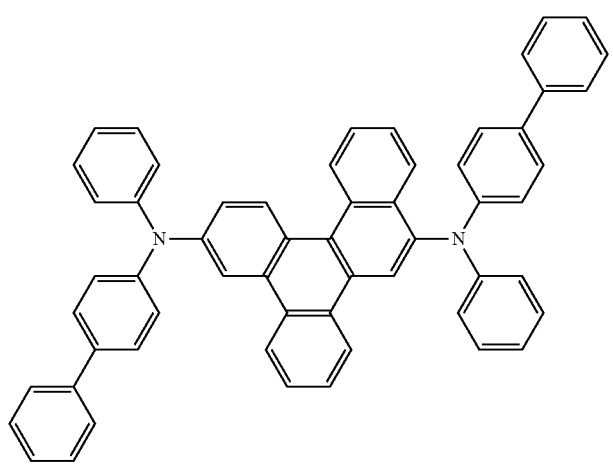
15

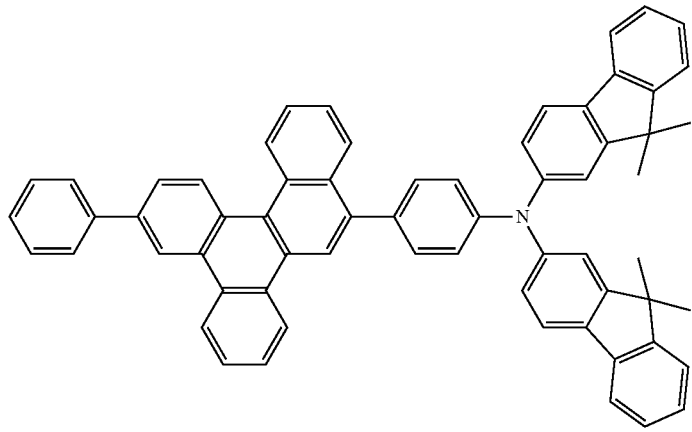

16

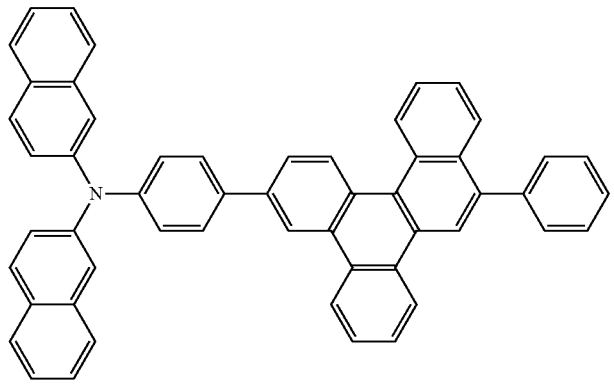

17

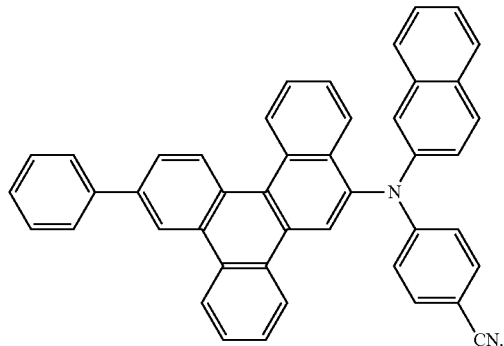

18

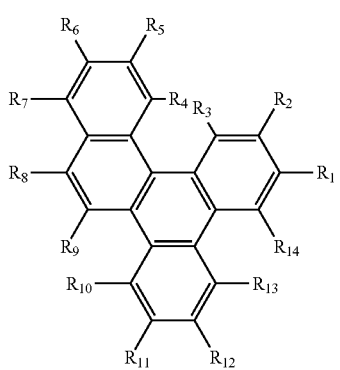

6. An organic light-emitting device comprising:
a first electrode;
a second electrode; and
an organic layer disposed between the first electrode and the second electrode,
wherein the organic layer comprises a first layer including the compound of Formula 1 of claim 1.

7. The organic light-emitting device of claim 6, wherein the first layer comprises an emission layer.

8. The organic light-emitting device of claim 6, wherein the first layer comprises an emission layer, and the compound of Formula 1 is used as a dopant.

9. The organic light-emitting device of claim 6, the first layer comprising an emission layer comprised of the compound of Formula 1 as a dopant and a compound represented by Formula 2 as a host:

[Formula 2]

R$_1$ to R$_{14}$ in Formula 2 are each independently selected from the group consisting of a hydrogen atom, a deuterium atom, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_3$-C$_{60}$ cycloalkyl group, a substituted or unsubstituted C$_1$-C$_{60}$ alkoxy group, a substituted or unsubstituted C$_6$-C$_{60}$ aryloxy group, a substituted or unsubstituted C$_6$-C$_{60}$ arylthio group, a substituted or unsubstituted C$_6$-C$_{60}$ aryl group, a substituted or unsubstituted C$_4$-C$_{60}$ heteroaryl group, a substituted or unsubstituted C$_6$-C$_{60}$ condensed polycyclic group, a halogen atom, a cyano group, a nitro group, a hydroxyl group, and a carboxyl group; and R$_8$ and R$_9$ are optionally linked together to form a saturated or unsaturated carbon ring.

10. The organic light-emitting device of claim 9, R$_1$ to R$_{14}$ in Formula 2 are each independently selected from the group consisting of a hydrogen atom, a deuterium atom, a cyano group, a halogen atom, a substituted or unsubstituted C$_1$-C$_{20}$ alkyl group, a substituted or unsubstituted C$_6$-C$_{40}$ aryl group, a substituted or unsubstituted C$_4$-C$_{40}$ heteroaryl group, and a substituted or unsubstituted C$_6$-C$_{40}$ condensed polycyclic group.

11. The organic light-emitting device of claim 9, R$_1$ to R$_{14}$ in Formula 2 are each independently selected from the group consisting of a hydrogen atom, a deuterium atom, a C$_1$-C$_{20}$ alkyl group, and groups represented by Formulae 4a to 4e below:

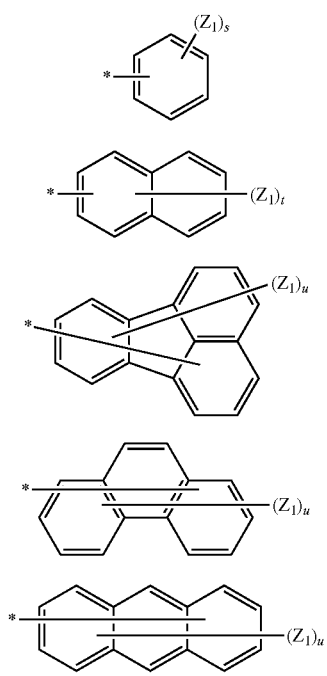

Z$_1$ in Formulae 4a to 4e is selected from the group consisting of a hydrogen atom, a deuterium atom, a substituted or unsubstituted C$_1$-C$_{20}$ alkyl group, a substituted or unsubstituted C$_6$-C$_{20}$ aryl group, a substituted or unsubstituted C$_4$-C$_{20}$ heteroaryl group, a substituted or unsubstituted C$_6$-C$_{20}$ condensed polycyclic group, a halogen atom, a cyano group, a nitro group, a hydroxyl group, and a carboxyl group;

s is an integer from 1 to 5;
t is an integer from 1 to 7;
u is an integer from 1 to 9; and
* indicates a binding site.

12. The organic light-emitting device of claim 9, wherein the compound of Formula 2 comprises one of the compounds below:

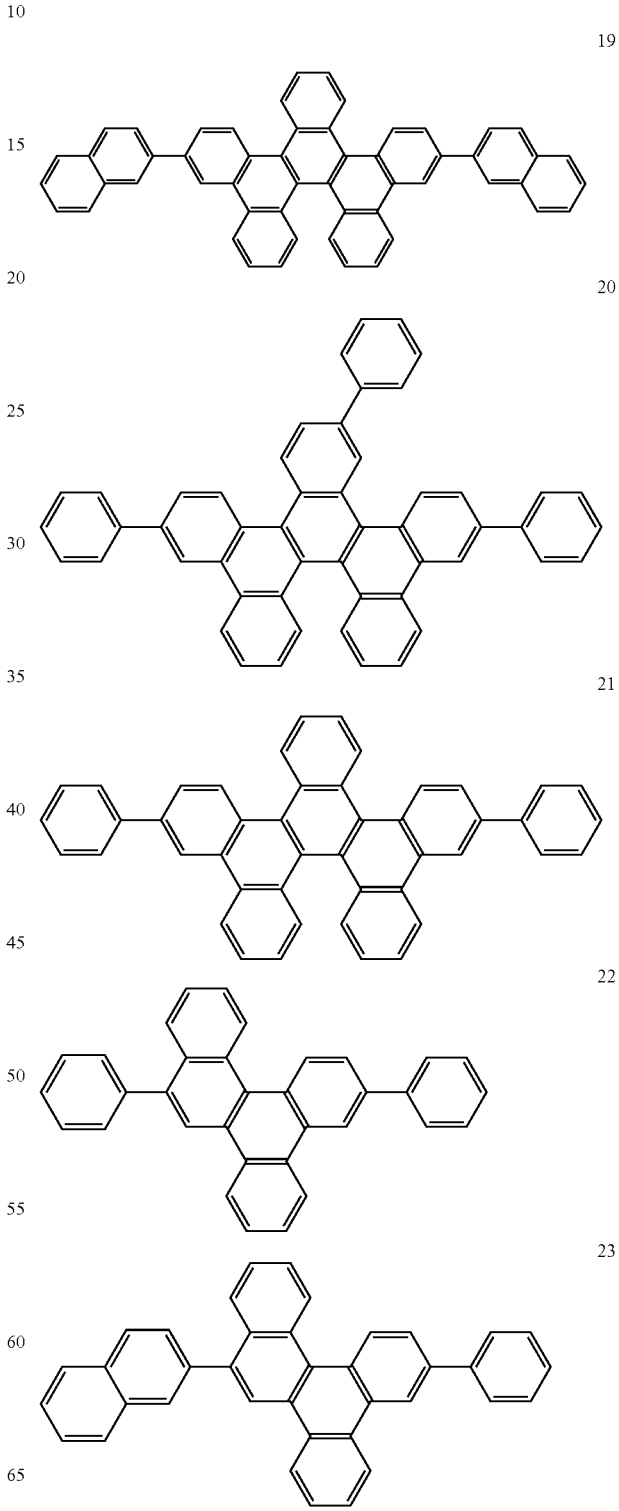

-continued

24

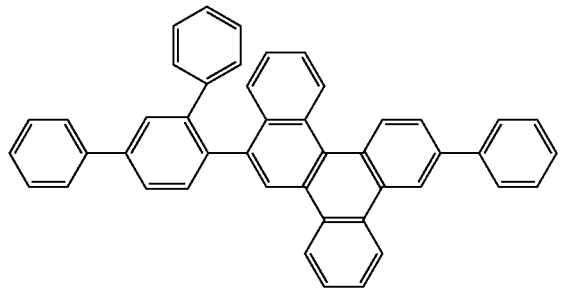

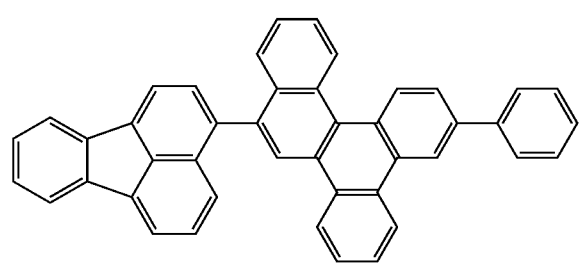
25

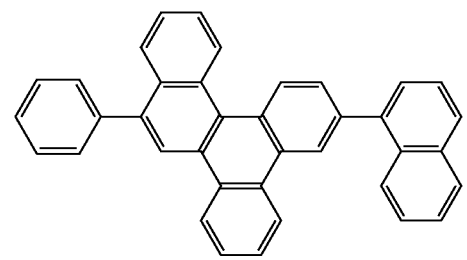
26

-continued

27

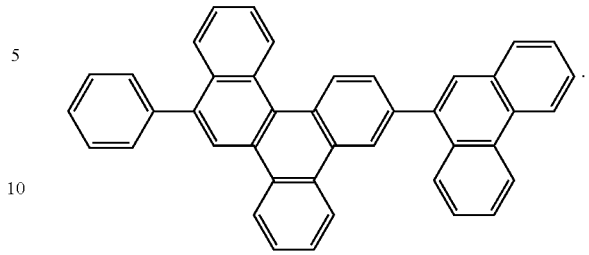

13. The organic light-emitting device of claim 9, wherein the emission layer comprises a blue emission layer, the compound of Formula 1 is used as a blue dopant, and the compound of Formula 2 is used as a blue host.

14. The organic light-emitting device of claim 6, wherein the first layer comprises an emission layer, and a red layer, a green layer, a blue layer, or a white layer of the emission layer contains a phosphorescent compound.

15. The organic light-emitting device of claim 6, wherein the organic layer further comprises a hole injection layer, a hole transport layer, a functional layer having both hole injection and hole transport capabilities, an emission layer, a hole blocking layer, an electron transport layer, an electron injection layer, or a combination of at least two thereof.

16. The organic light-emitting device of claim 15, wherein at least one of the hole injection layer, the hole transport layer, and the functional layer having hole injection and hole transport capabilities further comprises a charge generating material.

17. The organic light-emitting device of claim 15, wherein the electron transport layer comprises an electron transporting organic material and a metal-containing material.

18. The organic light-emitting device of claim 17, wherein the metal-containing material comprises a lithium (Li) complex.

\* \* \* \* \*